(12) United States Patent
Mansson et al.

(10) Patent No.: US 8,410,044 B2
(45) Date of Patent: Apr. 2, 2013

(54) BACITRACIN ANTIBIOTICS

(75) Inventors: Martin Mansson, Oslo (NO); Christine Senstad, Hosle (NO)

(73) Assignee: Xellia Pharmaceuticals Aps (DK)

( * ) Notice: Subject to any disclaimer, the term of this patent is extended or adjusted under 35 U.S.C. 154(b) by 0 days.

(21) Appl. No.: 13/502,142

(22) PCT Filed: Sep. 30, 2010

(86) PCT No.: PCT/EP2010/064523
§ 371 (c)(1),
(2), (4) Date: Apr. 16, 2012

(87) PCT Pub. No.: WO2011/051073
PCT Pub. Date: May 5, 2011

(65) Prior Publication Data
US 2012/0202737 A1    Aug. 9, 2012

Related U.S. Application Data

(60) Provisional application No. 61/255,517, filed on Oct. 28, 2009.

(51) Int. Cl.
*A01N 37/18* (2006.01)
*A61K 38/04* (2006.01)
*A61K 38/12* (2006.01)
(52) U.S. Cl. ............. 514/1.1; 514/2.3; 514/2.4; 514/2.9
(58) Field of Classification Search .................. None
See application file for complete search history.

(56) References Cited

FOREIGN PATENT DOCUMENTS
WO    93/08822    5/1993
WO    97/47313    12/1997

OTHER PUBLICATIONS

Wagner et al, Rational design of bacitracin a derivatives by incorporating natural product derived heterocycles, Journal of the American Chemical Society, vol. 128 No. 32, 2006, p. 10513-10520.*
Chilton et al.; "The Unsaturated Norleucines of *Amanita solitaria*. Chemical and Pharmacological Studies."; Lloydia; 36(2); pp. 169-173; (1973).
Craig et al.; "Further Studies with the Bacitracin Polypeptides"; J. Org. Chem.; 22; pp. 1345-1353; (1957).
Ikai et al., "Total Structures and Antimicrobial Activity of Bacitracin Minor Components"; The Journal of Antibiotics; 48 (3); pp. 233-242; (1995).
International Search Report and Written Opinion; International Applicationn No. PCT/EP2010/064523; International Filing Date Sep. 30, 2010; Priority Date Oct. 28, 2009; Date of Mailing Feb. 1, 2011; 9 pages.
Kelly et al.; "2-Amino-4-methyl-5-hexenoic acid, a Naturally Occurring Antimetabolite antibiotic"; Canadian Journal of Chemistry; 47; pp. 2504-2506; (1969).
Kleinkauf et al.; "Nonribosomal Biosynthesis of Peptide Antibiotics"; Eur. J. Biochem.; 192; pp. 1-15; (1990).
Lee et al.; "Solid-Phase Total Synthesis of Bacitracin A"; J. Org. Chem; 61; pp. 3983-3986; (1996).
Mock et al.; "Stereoselective Incorporation of an Unsaturated Isoleucine Analogue into a Protein Expressed in *E. coli*"; Chem BioChem; 7(1); pp. 83-87; (2006).
Muramatsu et al.; "Finding of an Isoleucine Derivative of a Recombinant Protein for Pharmaceutical Use"; Journal of Pharmaceutical and Biomedical Analysis; 31; pp. 979-987; (2003).
Norwegian Office Action dated May 7, 2010, Application No. NO20093238 with English Translation; 6 pages.
Offenzeller et al.; "Biosynthesis of the Unusual Amino Acid (4R)-4-[(E)-2-Butenyl]-4-methyl-L-threonine of Cyclosporin A"; Journal of Biological Chemistry; 268(35); pp. 26127-26134; (1993).
Sugiura et al.; "B-Methylnorleucine, An Antimetabolite Produced by *Serratia marcescens*"; The Journal of Antibiotics; 34(10); pp. 1278-1282; (1982\1).
Takeuchi et al., "2-Amino-5-Methyl-5-Hexenoic Acid, a Methionine Analog Produced by *Streptomyces* SP. MF374-C4"; Journal of Antibiotics; 32(11); pp. 1118-1124; (1979).
Wagner et al.; "Rational Design of Bacitracin A Derivatives by Incorporating Natural Product Derived Heterocycles"; J. Am. Chem Soc.; 128; pp. 10513-10520p (2006).
Saberwal et al, "Cell-lytic and antibacterial peptides that acvt by perturbing the barrier function of membranes:facets of their conformational features, structure-function correlations and membrane-perturbing abilities", Biochemica et Biophysica Acta MR Reviews on Biomembranes, vol. 1197, No. 2 (Jun. 29, 1994).

* cited by examiner

*Primary Examiner* — Anish Gupta
*Assistant Examiner* — Sergio Coffa
(74) *Attorney, Agent, or Firm* — Cantor Colburn LLP

(57) ABSTRACT

The invention concerns new Bacitracin compounds containing methylene-isoleucine.

15 Claims, 17 Drawing Sheets

BACITRACIN ANTIBIOTICS

FIELD OF INVENTION

The present invention relates to new compounds with antibiotic activity.

BACKGROUND OF INVENTION

A group of closely related peptide antibiotics naturally produced by *Bacillus subtilis* and *Bacillus licheniformis* are called Bacitracins. Bacitracins are generally active against many Gram positive and a few Gram negative bacteria species.

Several Bacitracins have been identified of which Bacitracin A is of primary importance and is highly active (Biochemistry, vol. 39 no 14, 2000, page 4037-45 by Epperson and Ming). Bacitracin A is a branched cyclic dodecapeptidolactam antibiotic that is synthesized via the thiotemplate mechanism of non-ribosomal peptide synthesis (J. Am. Chem. Soc. vol. 128, 2006, page 10513-10520 by Wagner et al and Eur J Biochem, vol. 192 no. 1, 1990, page 1-15 by Kleinkauf and von Döhren).

The primary structure of Bacitracin A is $NH_2$-L-$Ile_1$-L-$thiazoline_2$-L-$Leu_3$-D-$Glu_4$-L-$Ile_5$-L-$Lys_6$-D-$Orn_7$-L-$Ile_8$-D-$Phe_9$-L-$His_{10}$-D-$Asp_{11}$-L-$Asn_{12}$-COOH which is cyclized between the $\epsilon$-amino group of L-$Lys_6$ and the R-carboxyl group of L-$Asn_{12}$ (J. Am. Chem. Soc. vol 128 page 10513-10520, 2006 by Wagner et al).

Ming et al (Journal of Inorganic Biochemistry, vol. 91, 2002) described Bacitracins as peptide compounds with the following formula:

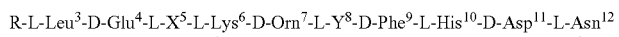

wherein
X is Ile or Val and
Y is Ile or Val

Notably, $R_1$ and $R_3$ are the N-terminal moieties of active Bacitracins, while $R_4$ and $R_5$ are oxidized N-terminal moieties of less active Bacitracins. $R_2$ is however an inactive stereoisomer.

PRIOR ART

Ikai et al suggested that the activity of Bacitracins may depend on the hydrophobicity:

"Comparison of the MICs and the proposed structures of the minor components suggest that the location of the valine affects the activity of each component in the following decreasing order: N-terminus, the seven membered peptide ring, and the side chain peptide moiety. Because this order is related to the elution order of the minor components on the HPLC, the activity may depend on the hydrophobicity of the respective component." (see Journal of Antibiotics, vol. 48 no. 3, 1995 page 233-242 by Ikai et al).

Wagner et al suggested incorporating new heterocycles into Bacitracin A in order to overcome existing limitations for the application of Bacitracin (Journal of the American Chemical Society, vol. 128 no 32, 2006, page 10513-10520).

Several non-ribosomally synthesized peptides comprise unusual amino acids. For example cyclosporin A comprises 2(S)-Amino-3(R)-Hydroxy-4(R)-Methyl-6(E)-Octenoic acid which is crucial for binding to the intracellular receptor for cyclophilin, and thus for its immunosuppressive activity (Journal of Biological Chemistry, vol. 268 no 35, 1993 by Offenzeller et al).

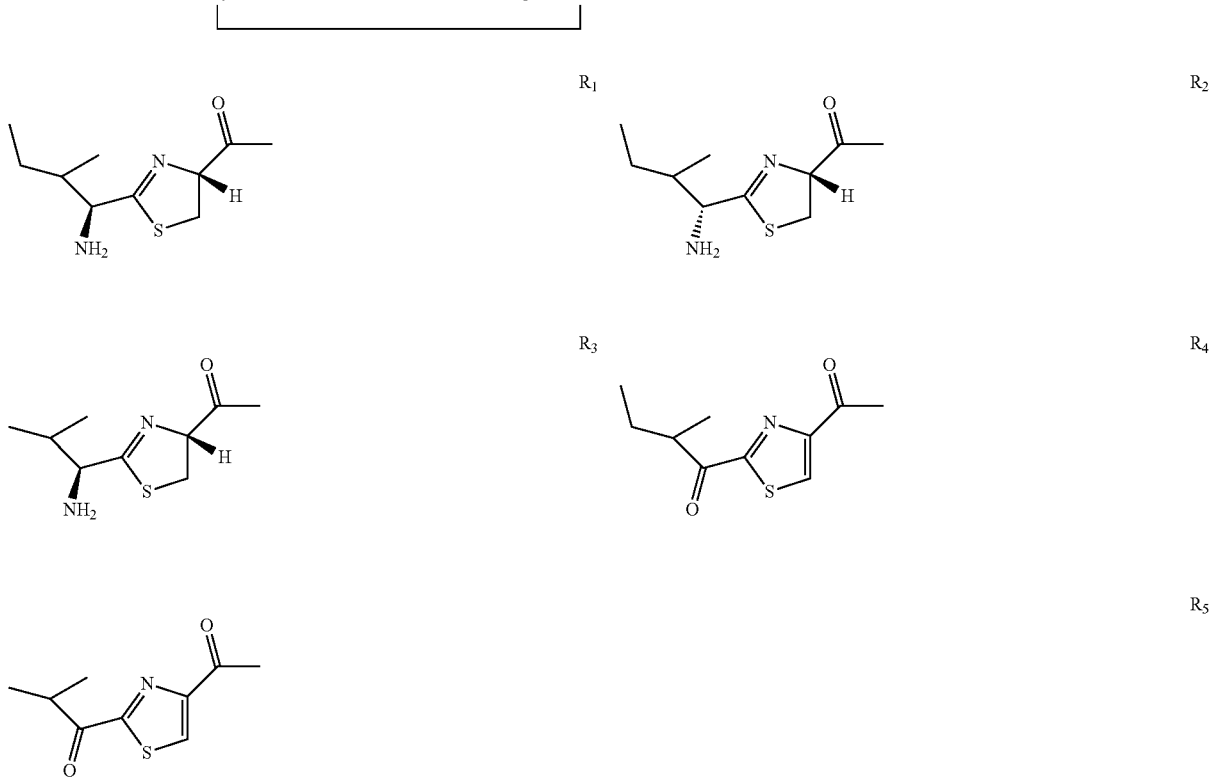

Several uncommon amino acids resembles the structure of Isoleucine:

2-Amino-5-Methyl-5-Hexenoic acid, a new methionine analog, was isolated from a fermentation broth of *Streptomyces* (Journal of Antibiotics vol. 32 no. 11, page 1118-1124, 1979 by Takeuchi et al).

4 methylene-norleucine and 2-aminohept-6-enoic acid are compounds with the formula: $C_7H_{13}NO_2$.

4 methyl-norleucine is an isoleucine derivative which can be incorporated into a recombinant protein. (J Pharm Biomed Anal, vol 31. no. 5, 2003, page 979-987 by Muramatsu et al).

2-amino-3-methyl-4-pentenoic acid is an unsaturated isoleucine analogue which can be incorporated into proteins (Chembiochem vol. 7 no. 1, 2006, page 83-87 by Mock et al).

The unsaturated norleucines of *Amanita solitaria*. Chemical and pharmacological studies discloses a 2-Amino-Hex-5-enoic acid (Lloydia vol. 36 no. 2, 1973, page 69-73 by Chilton et al).

Beta-methylnorleucine, an antimetabolite produced by *Serratia marcescens* (J Antibiot, vol. 34 no. 10, 1981 page 1278-82 by Sugiura et al)

SUMMARY OF THE INVENTION

In one aspect, this invention concerns new Bacitracin compounds. More specifically it concerns new Bacitracin compounds comprising a hitherto unknown amino acid side chain.

In *Bacillus subtilis* and *Bacillus licheniformis*, without being bound by theory, we speculate that this side chain is resulting from a chemical modification on Bacitracin or from incorporation of a hitherto unknown natural amino acid.

The systematic name of an α-amino acid compound comprising the new side chain is 2-amino-3-methyl-5-hexenoic acid and its molecular formula is $C_7H_{13}NO_2$.

We propose and use the name 5-Methylene-Isoleucine for 2-amino-3-methyl-5-hexenoic acid. Accordingly, the 5-Methylene-Isoleucine side chain has the structure —CH(CH$_3$)CH$_2$CH=CH$_2$ Thus, the invention concerns new Bacitracin compounds with antibacterial activity comprising at least one 5-Methylene-Isoleucine residue. Such Bacitracins comprise at least one side chain of 5-Methylene-Isoleucine. The side chain of 5-Methylene-Isoleucine could be represented:

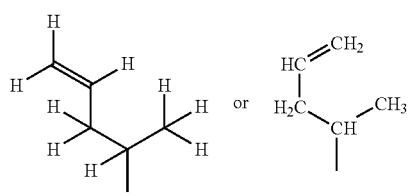

The invention concerns Bacitracin compounds with antibacterial activity comprising one or more side chains of 5-Methylene-Isoleucine.

The Bacitracins according to the invention comprise at least one 5-Methylene-Isoleucine residue in position 1 and/or 5 and/or 8. Such compounds have the following structure:

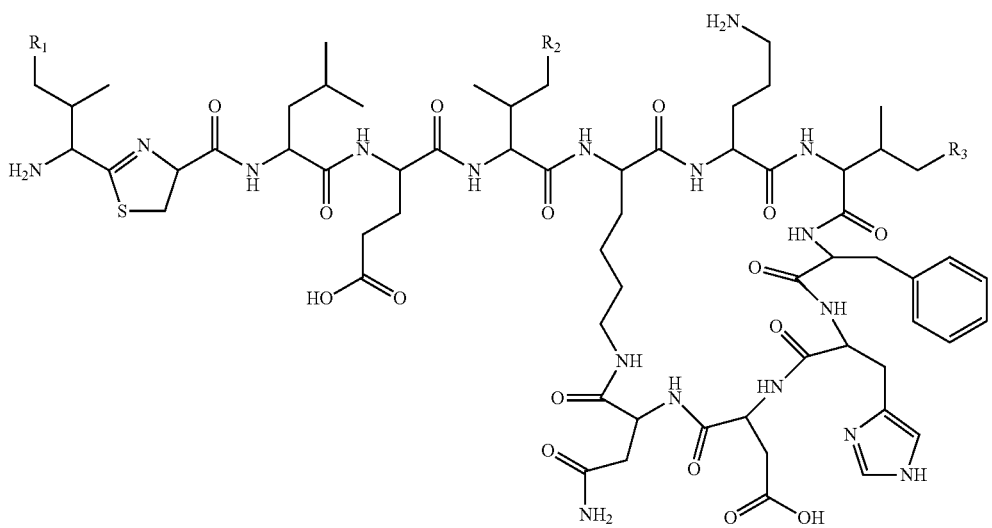

wherein at least one of $R_1$, $R_2$ and $R_3$ is —CH=CH$_2$, and wherein $R_1$, $R_2$ and $R_3$ are independently —H, —CH$_3$, or —CH=CH$_2$ The structure above should be interpreted as covering Bacitracin A if $R_1$, $R_2$ and $R_3$ were all —CH$_3$.

Accordingly, Bacitracin A would be represented:

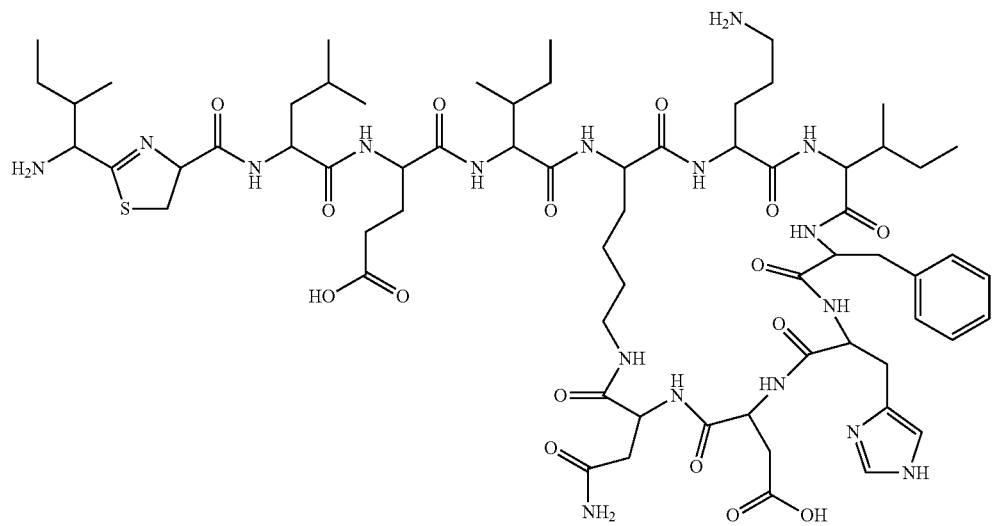 [SMILES: CCC(C)C(N)C1=NC(C(=O)NC(CC(C)C)C(=O)NC(CCC(=O)O)C(=O)NC(C(=O)NC2CCCCNC(=O)C(CC(N)=O)NC(=O)C(CC(=O)O)NC(=O)C(Cc3c[nH]cn3)NC(=O)C(Cc3ccccc3)NC(=O)C(C(C)CC)NC(=O)C(CCCN)NC2=O)C(C)CC)CS1]

We propose and use the name Bacitracin J1 for Bacitracins according to the invention comprising a 5-Methylene-Isoleucine residue in position 5. This nomenclature is based on elution order from a C18-column.

We propose and use the name Bacitracin J2 for Bacitracins according to the invention comprising a 5-Methylene-Isoleucine residue in position 8. This nomenclature is based on elution order from a C18-column.

We propose and use the name Bacitracin J3 for Bacitracins according to the invention comprising a 5-Methylene-Isoleucine residue in position 1. This nomenclature is based on elution order from a C18-column.

We propose and use the name Bacitracin K1 for Bacitracins according to the invention comprising 5-Methylene-Isoleucine residues in position 5 and 8. This nomenclature is based on expected elution order from a C18-column.

We propose and use the name Bacitracin K2 for Bacitracins according to the invention comprising 5-Methylene-Isoleucine residues in position 1 and 5. This nomenclature is based on expected elution order from a C18-column.

We propose and use the name Bacitracin K3 for Bacitracins according to the invention comprising 5-Methylene-Isoleucine residues in position 1 and 8. This nomenclature is based on expected elution order from a C18-column.

We propose and use the name Bacitracin L for Bacitracins according to the invention comprising 5-Methylene-Isoleucine residues in position 1, 5 and 8. This nomenclature is based on expected elution order from a C18-column.

The aspects of the invention may be obtained by the features as set forth in the following description of the invention and/or the appended patent claims.

DETAILED DESCRIPTION OF THE INVENTION

Definitions

"Bacitracins" are peptide compounds comprising the following structure (with amino acid residue numbering in superscript):

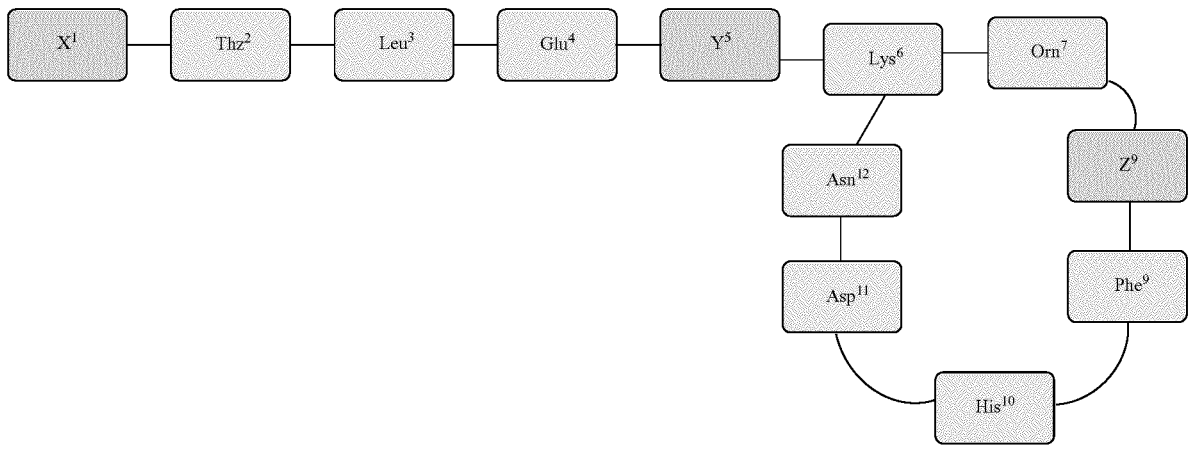

wherein X is

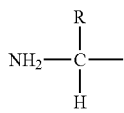

and wherein R is the side chain of the amino acid residue of Isoleucine, Valine or 5-Methylene-Isoleucine;
and wherein Y and Z are independently the amino acid residue of Isoleucine, Valine or 5-Methylene-Isoleucine;
and wherein Thz is a Thiazoline ring

2' coupled to X and 4' coupled to the α-carbon in Leu;
and wherein
Leu is a Leucine amino acid residue
Glu is a Glutamine amino acid residue
Lys is a Lysine amino acid residue forming peptide bonds with Y and Orn while its ε-amine is coupled to the α-carboxyl group of Asparagine by a peptide bond
Orn is an Ornithine amino acid residue
Phe is a Phenylalanine amino acid residue
His is a Histidine amino acid residue
Asp is an Aspartic acid amino acid residue
Asn is an Asparagine amino acid residue forming peptide bond with Asp while its α-carboxyl group is coupled to the ε-amine of Lysine by a peptide bond;

When used in this application; "Bacitracins" is meant to embrace any compound having the structure above regardless of the production method. Thus, the term "Bacitracins" includes the antibiotic compounds naturally produced by *Bacillus licheniformis* but also in vitro produced compounds (synthetic) and semisynthetic compounds having the primary structure above. "Bacitracins" is also meant to embrace any compound having the structure above regardless of the charge which varies with pH. "Bacitracins" is also meant to embrace any compound having the primary structure above regardless of the stereochemistry. "Bacitracins" is also meant to embrace salts and hydrates of the compounds having the primary structure above.

"Bacitracins comprising at least one 5-Methylene-Isoleucine residue" is meant to embrace any Bacitracin comprising the structure that would be generated if a Isoleucine or Valine residue(s) was substituted with 5-Methylene-Isoleucine residue(s) in position 1 and/or 5 and/or 8.

"Bacitracins comprising a 5-Methylene-Isoleucine residue" is meant to embrace any Bacitracin displaying the structure that would be generated if an Isoleucine or Valine residue was substituted with 5-Methylene-Isoleucine residue position 1 or 5 or 8.

"Bacitracins comprising the side chain of at least one 5-Methylene-Isoleucine" is meant to embrace "Bacitracins comprising at least one 5-Methylene-Isoleucine residue"

When the N-terminal amino group and/or the Thiazoline ring of Bacitracins is oxidized, a substantial amount of the antibacterial activity is lost. For example the low activity compound Bacitracin F, comprises a keto-thiazole moiety instead of the amino-thiazoline moiety (J. Org. Chem., vol. 22, 1957, page 1345-1353 by Craig et al).

Amino acids in D-configuration are common in non-ribosomally synthesized bacterial peptides and less common in ribosomally synthesized proteins. For example in Bacitracins, the amino acid residues in position 4, 7, 9 and 11 are usually in D-configuration (Glu, Orn, Phe and Asp).

5-Methylene-Isoleucine comprises two chiral carbon atoms which independently could be in R or S configuration.

An "Amino acid residue" is the unit in a peptide which comprises
—NH—CHR—COOH (C-terminal residue) or
NH$_2$—CHR—CO— (N-terminal residue) or
—NH—CHR—CO— (internal residue)
wherein R is
—H in Glycine,
—CH$_3$ in Alanine,
—OH in Serine,
—CH$_2$SH in Cysteine,
—CH(CH$_3$)CH$_2$CH$_3$ in Isoleucine,
—CH$_2$CH(CH$_3$)$_2$ in Leucine
—CH(CH$_3$)$_2$ in Valine
etc.

An "Amino acid side chain" is the R-group of an "Amino acid residue". For example, the R-group is
—CH(CH$_3$)CH$_2$CH=CH$_2$ in 5-Methylene-Isoleucine
—CH(CH$_3$)CH$_2$CH$_3$ in Isoleucine,
—CH$_2$CH(CH$_3$)$_2$ in Leucine
—CH(CH$_3$)$_2$ in Valine "Antibacterial activity" is any activity which
inhibits the growth, metabolism or reproduction of bacteria, or
increases the mortality of bacteria, or
reduces the pathogenicity of bacteria.

Potency is the in vitro antibacterial activity. It can be measurered and expressed as IU/mg.

The "positions" of the amino acid residues in Bacitracins are numbered from the N-terminal which can be Isoleucine, Valine or 5-Methylene-Isoleucine in position 1 (the left end in all figures showing Bacitracins in this application). Hence, Lys is in position number 6 and Asn is in position number 12.

In Bacitracins, the "position 1" is special, because this amino acid residue is partly incorporated into the Thiazoline ring. Thus the amino acid residue in position 1 in Bacitracins does not comprise the usual N-terminal unit:

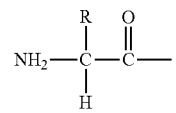

but comprises instead:

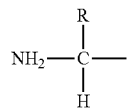

coupled to Thiazoline or oxidized derivatives thereof.

A "composition" is any mixture comprising more than two different compounds. For example, a mixture of two active pharmaceutical ingredients, or a mixture of an active pharmaceutical ingredient and one or more pharmaceutical excipients.

The term "component" or "components" used in this application is referring to a specific compound in a composition. Accordingly, "Minor components" are compounds found in relatively small amounts in a composition.

A "pharmaceutical composition" is any composition suitable for use in vivo. Such compositions can thus be administered cutaneously, subcutaneously, intravenously, parenterally, orally etc.

The invention concerns new Bacitracin compounds comprising the side chain of at least one 5-Methylene-Isoleucine residue.

More specifically, the invention concerns new Bacitracin compounds with antibacterial activity comprising at least one 5-Methylene-Isoleucine residue.

Even more specifically it concerns new Bacitracin compounds with improved antibacterial activity comprising at least one 5-Methylene-Isoleucine residue(s) in position 1 or 5 or 8.

Even more specifically, it concerns new Bacitracin compounds with antibacterial activity comprising one 5-Methylene-Isoleucine residue in position 1 or 5 or 8.

The invention also concerns new Bacitracin compounds with antibacterial activity comprising two 5-Methylene-Isoleucine residues in position 1 and 5.

The invention also concerns new Bacitracin compounds with antibacterial activity comprising two 5-Methylene-Isoleucine residues in position 1 and 8.

The invention also concerns new Bacitracin compounds with antibacterial activity comprising two 5-Methylene-Isoleucine residues in position 5 and 8.

The invention also concerns new Bacitracin compounds with antibacterial activity comprising three 5-Methylene-Isoleucine residues in position 1 and 5 and 8.

The Bacitracins comprising at least one 5-Methylene-Isoleucine residue in position 1, 5 or 8 can be used for inhibiting unwanted bacterial growth both in vitro and in vivo. These compounds can thus have therapeutic effect if administered to an animal or a human with a bacterial infection.

When 5-Methylene-Isoleucine is incorporated in Bacitracins at position 1, 5 or 8, the resulting amino acid side chain is unsaturated and comprises 5 carbon atoms. The side chains of Isoleucine and Valine residues comprise 4 or 3 carbon atoms, respectively. The elution order from a C18-column is Bacitracin A, Bacitracin J1, Bacitracin J2 and Bacitracin J3 (see Chromatograms in FIG. 1). Thus it is reasonable that substitution of a Isoleucine side chain with the 5-Methylene-Isoleucine side chain results in more hydrophobic Bacitracins.

| Valine side chain | Isoleucine side chain | 5-Methylene-Isoleucine side chain |
|---|---|---|
| H$_3$C\_CH\_CH$_3$ | CH$_3$—H$_2$C\_CH\_CH$_3$ | CH$_2$=HC—H$_2$C\_CH\_CH$_3$ |

Preferred compounds of this invention are Bacitracin J1-3 naturally produced by *Bacillus licheniformis*; e.g. Bacitracin J1, Bacitracin J2 and Bacitracin J3 as visualized in FIGS. 8A-8C.

Preferred compounds of this invention are Bacitracins J1-3 with the same stereochemistry as the natural fermentation product Bacitracin A.

Preferred compounds of this invention are Bacitracins J1-3, Bacitracins K1-3 or Bacitracin L with amino acid residues in position 4, 7, 9 and 11 are in D-configuration (Glu, Orn, Phe and Asp).

Abbreviations:
Mil=5-Methylene-Isoleucine
Thz=Thiazoline
Ala=Alanine
Arg=Arginine
Asn=Asparagine
Asp=Aspartic acid
Cys=Cysteine
Gln=Glutamine
Glu=Glutamate
Phe=Phenylalanine
Gly=Glycine
His=Histidine
Ile=Isoleucine
Lys=Lysine
Leu=Leucine
Met=Methionine
Pro=Proline
Ser=Serine
Thr=Threonine
Trp=Tryptophan
Tyr=Tyrosine
Val=Valine
LC-MS=liquid chromatography-mass spectrometry
NMR=Nuclear Magnetic Resonance
V=volume
M=Molar Production of the Bacitracins disclosed in this application, can be done by solid phase synthesis as described in J Org Chem, vol. 61 no. 12, 1996, page 3983-3986 by Lee et al.

WO199747313 describes synthesis of Bacitracin peptides which could be used to produce the new Bacitracins of this invention.

Alternatively, the new Bacitracins can be produced from Bacitracin producing strains of *Bacillus licheniformis* and obtained by purification.

Figure 1A:
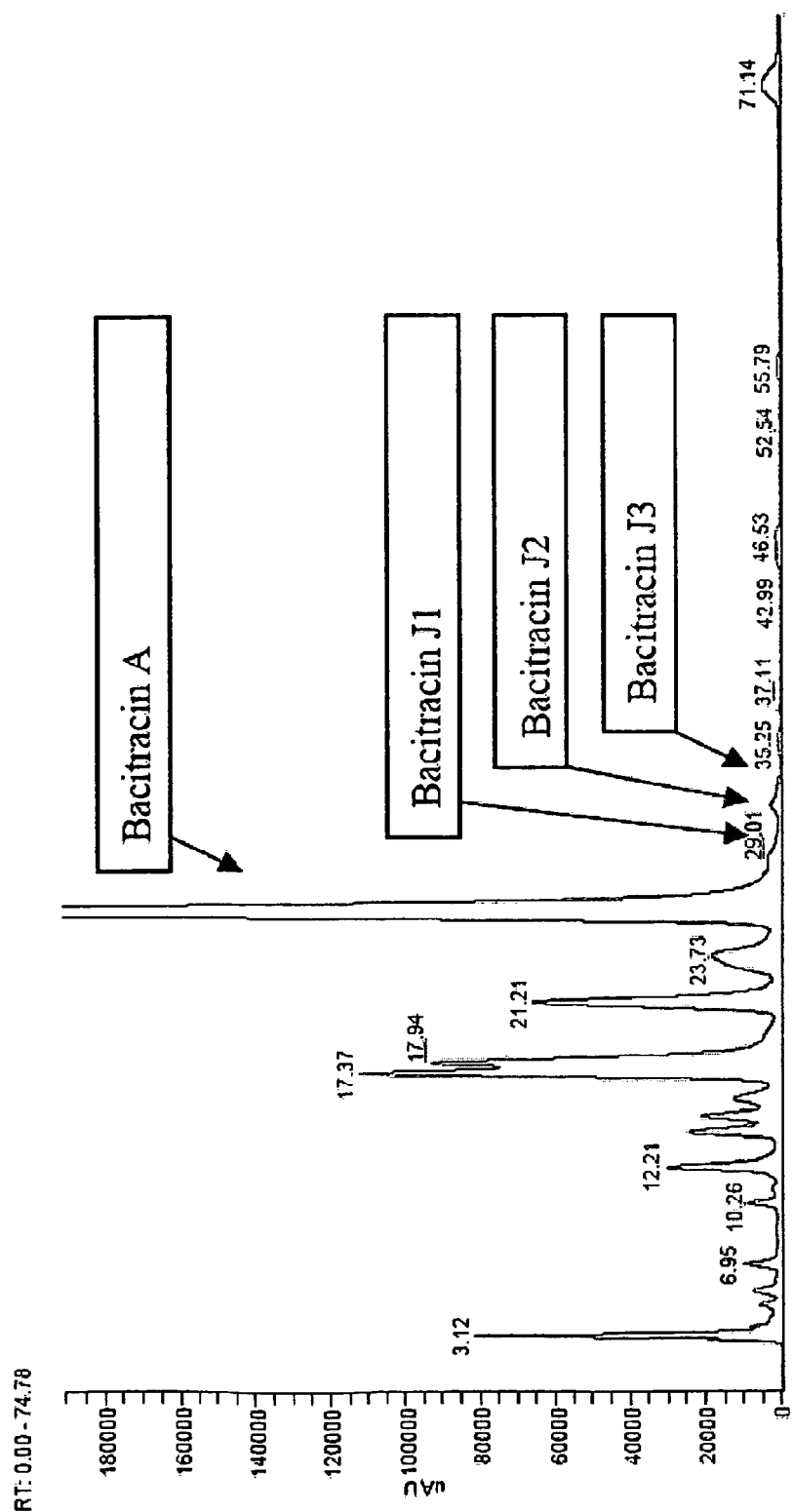
FIG. 1A shows an UV chromatogram at 254 nm of a commercial lot from Axellia (BANN 211412) obtained using an YMC-Pack Pro C18-column (5 µm, 250×2.0 mm) at 30° C. The mobile phase consisted of methanol/acetonitrile/0.1 M ammonium acetate pH 6.0/water 58:5:10:27, v/v/v/v. Isocratic conditions was used at the flow rate 0.2 ml/min. The injection volume was 10 µl. Except for Bacitracin A, three minor components denoted Bacitracin J1, Bacitracin J2 and Bacitracin J3, all with molecular weights 12 Da more than Bacitracin A, are marked.

The invention is defined by the claims and not by the following illustrative examples:

EXAMPLES

Experiment 1

LC-MS$^n$

The samples used were commercial lots from Axellia Pharmaceuticals. The samples were dissolved in water to concentration 2 mg/ml and were then filtered through 0.45 μm filters (VWR) before LC-MS$^n$ analysis.

The Surveyor HPLC system (Thermo Fisher) consisted of a quarternary pump, degasser, thermostated autosampler (set to 5° C.), thermostated column compartment (set to 30° C.) and a diode-array detector (set to 254 nm). The HPLC conditions were the same as described in Govaerts et al (Rapid Communications in Mass Spectrometry, vol. 17, no 12, page 1366-1379). An YMC-Pack Pro C18-column (5 μm, 250×2.0 mm) was used. The mobile phase consisted of methanol/acetonitrile/0.1 M ammonium acetate pH 6.0/water 58:5:10: 27, v/v/v/v. The 0.1 M ammonium acetate solution was adjusted to pH 6.0 by adding 0.1 M acetic acid. Isocratic conditions was used at the flow rate 0.2 ml/min. The injection volume was 10 μl. An LXQ linear ion trap mass spectrometer (Thermo Fisher) equipped with an ESI interface was connected to the HPLC system. Tuning was performed on the doubly protonated molecular ion ([M+2H]$^{2+}$) of Bacitracin A. The ESI parameters were set as follows: sheath gas 35 (arbitrary units), auxiliary gas 10 (arbitrary units), spray voltage 5.0 kV, capillary temperature 320° C., capillary voltage 9.0 V, tube lens voltage 95 V. The MS parameters were set as follows: RF lens offset −4.25 V, lens 0 voltage −3.0 V, multipole 0 offset −4.5 V, lens 1 voltage −8.0 V, gate lens voltage −56 V, multipole 1 offset −9.5 V, multipole RF amplitude 400 V, front lens voltage −6.5 V. LC-MS/MS- and LC-MS$^3$-analyses were performed with isolation widths 3 and collision energies 16%.

Results

Figure 1B:
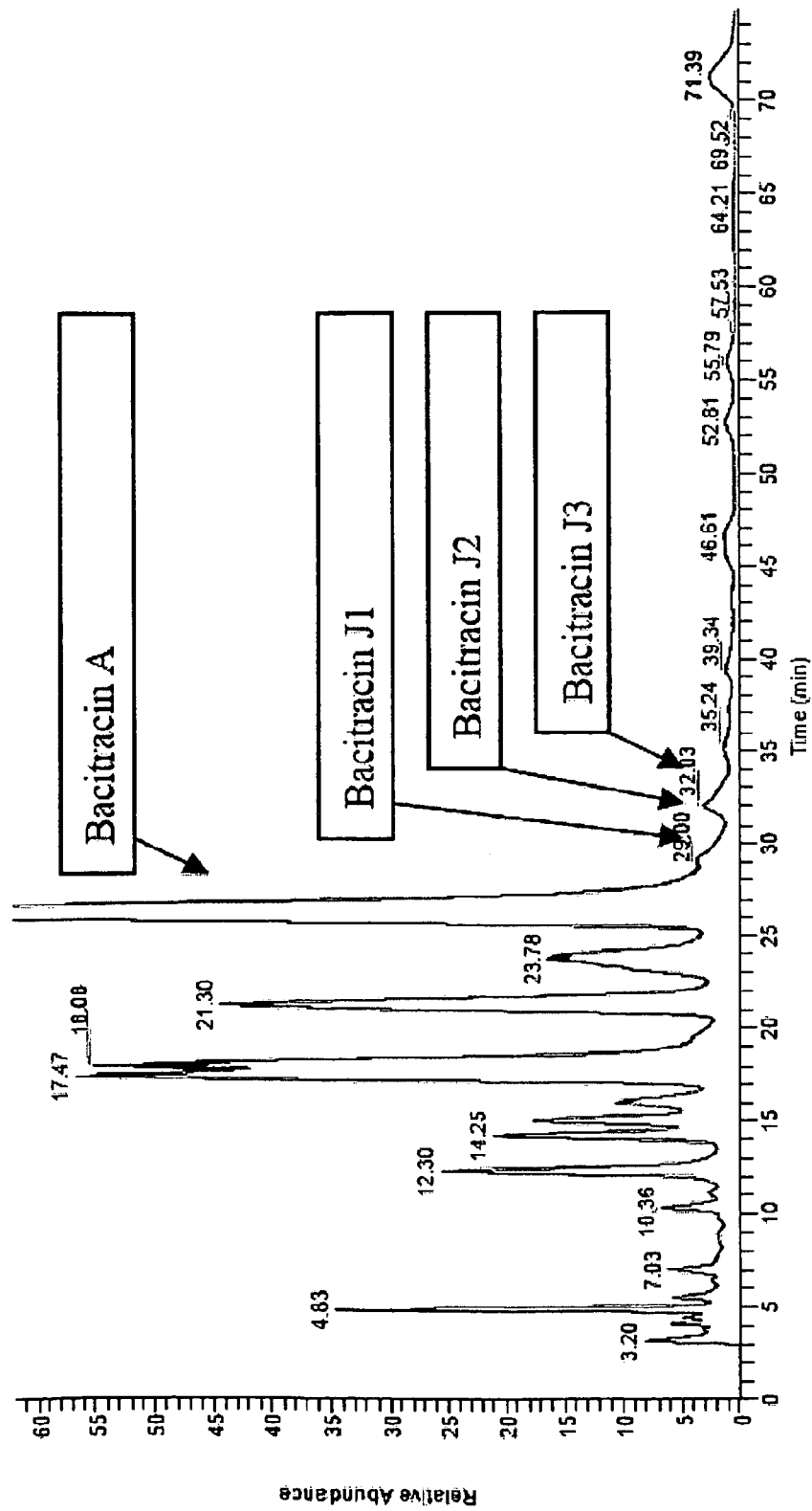
FIG. 1B shows the corresponding MS TIC chromatogram with denotations as in FIG. 1A.

The UV- and MS-chromatograms of a typical lot (BANN 211412) from Axellia Pharmaceuticals are shown in FIG. 1A-B. The UV-chromatogram is very similar to the corresponding chromatogram of this lot using the LC-MS incompatible Ph.Eur. HPLC method. Except for Bacitracin A, three minor components denoted Bacitracin J1, Bacitracin J2 and Bacitracin J3, all with molecular weights 12 Da more than Bacitracin A, are marked in FIG. 1. The structural elucidation of these three components will be described in this application and their structure will give the rationale for their denotations.

Bacitracin A

Figure 2A:
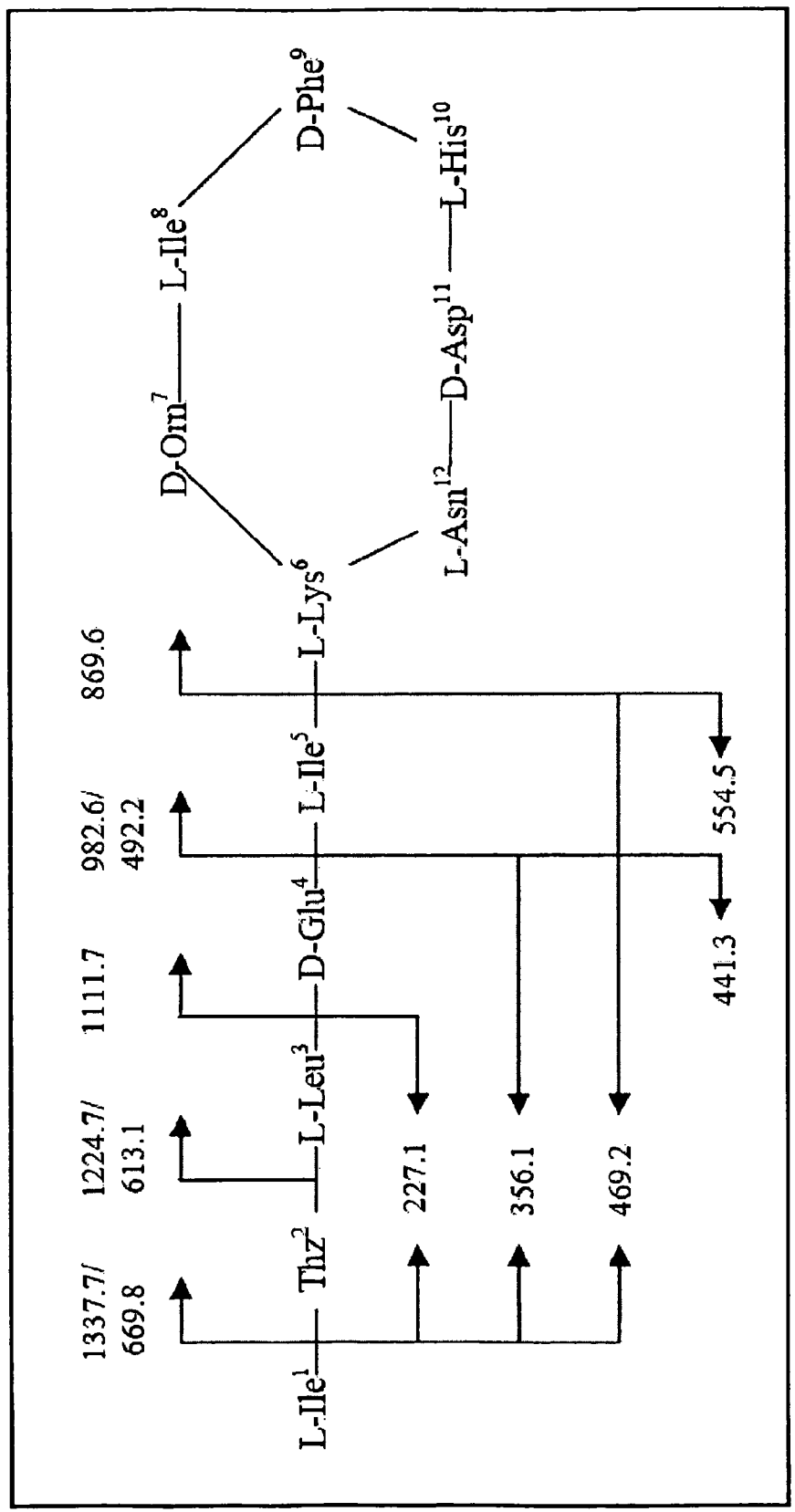
FIG. 2A shows the structure of Bacitracin A, where fragment ion assignments are done for characteristic ions in the product ion spectrum below.
Figure 2B:
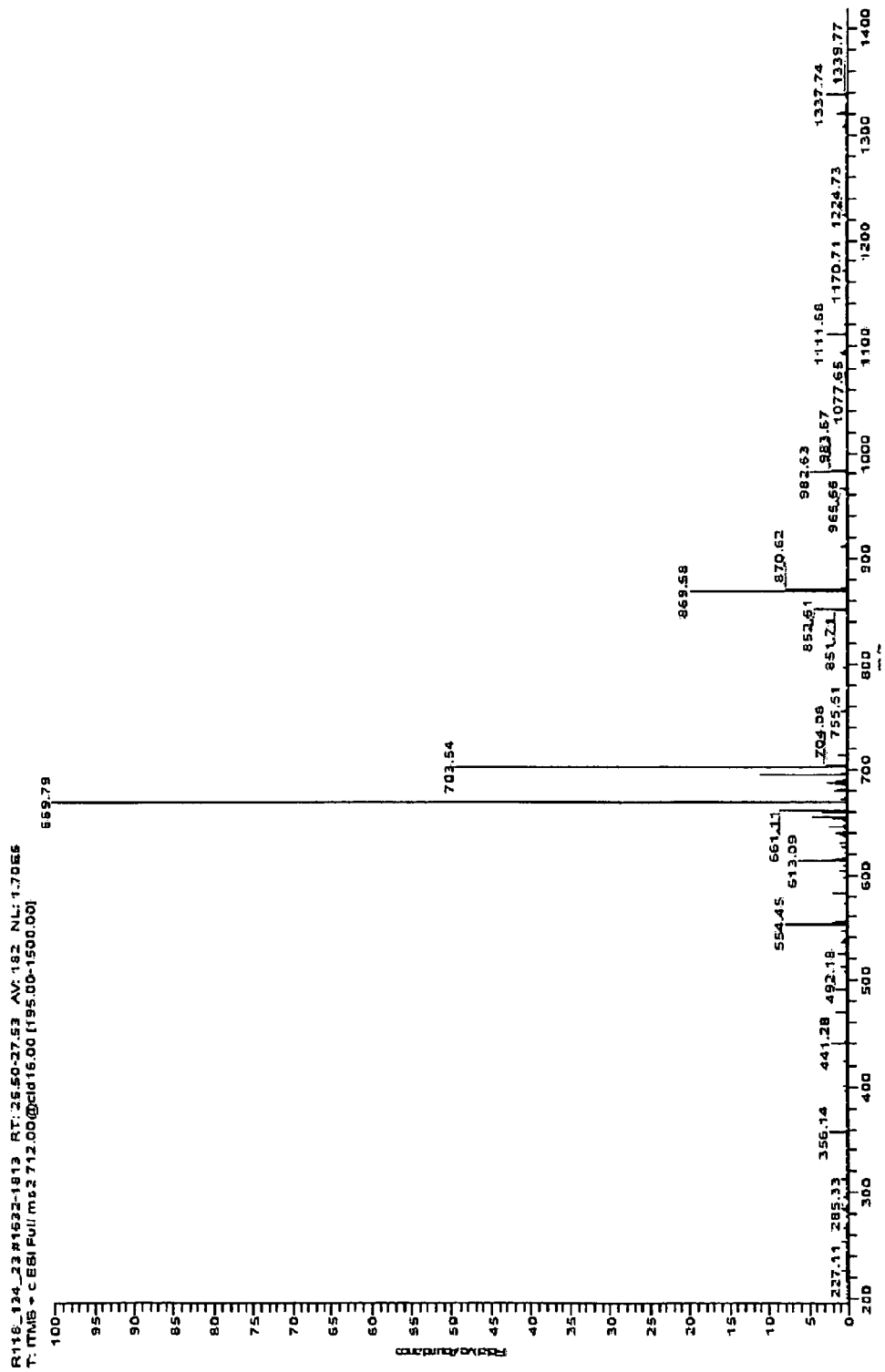
FIG. 2B shows the product ion (MS/MS) spectrum of Bacitracin A, where the precursor ion at m/z 712.0 ([M+2H]$^{2+}$) was isolated and fragmented.

The doubly protonated molecular ion ([M+2H]$^{2+}$, m/z 712.0) was isolated and fragmented and the resulting product ion (MS/MS) spectrum is shown in FIG. 2B.

The spectrum contains a full set of y″ ions with m/z 1337.7/ 669.8$^{2+}$ (loss of Ile), m/z 1224.7/613.1$^{2+}$ (loss of IleThz), m/z 1111.7 (loss of IleThzLeu), m/z 982.6/492.2$^{2+}$ (loss of IleThzLeuGlu) and m/z 869.6 (loss of IleThzLeuGluIle). These fragment assignments are visualized in FIG. 2A. In addition to the b ions with m/z 554.5 (IleThzLeuGluIle) and m/z 441.3 (IleThzLeuGlu), fragment ions resulting from pairs of bond cleavages can be seen at m/z 227.1 (ThzLeu), m/z 356.1 (ThzLeuGlu) and at m/z 469.2 (ThzLeuGluIle).

Figure 3A:
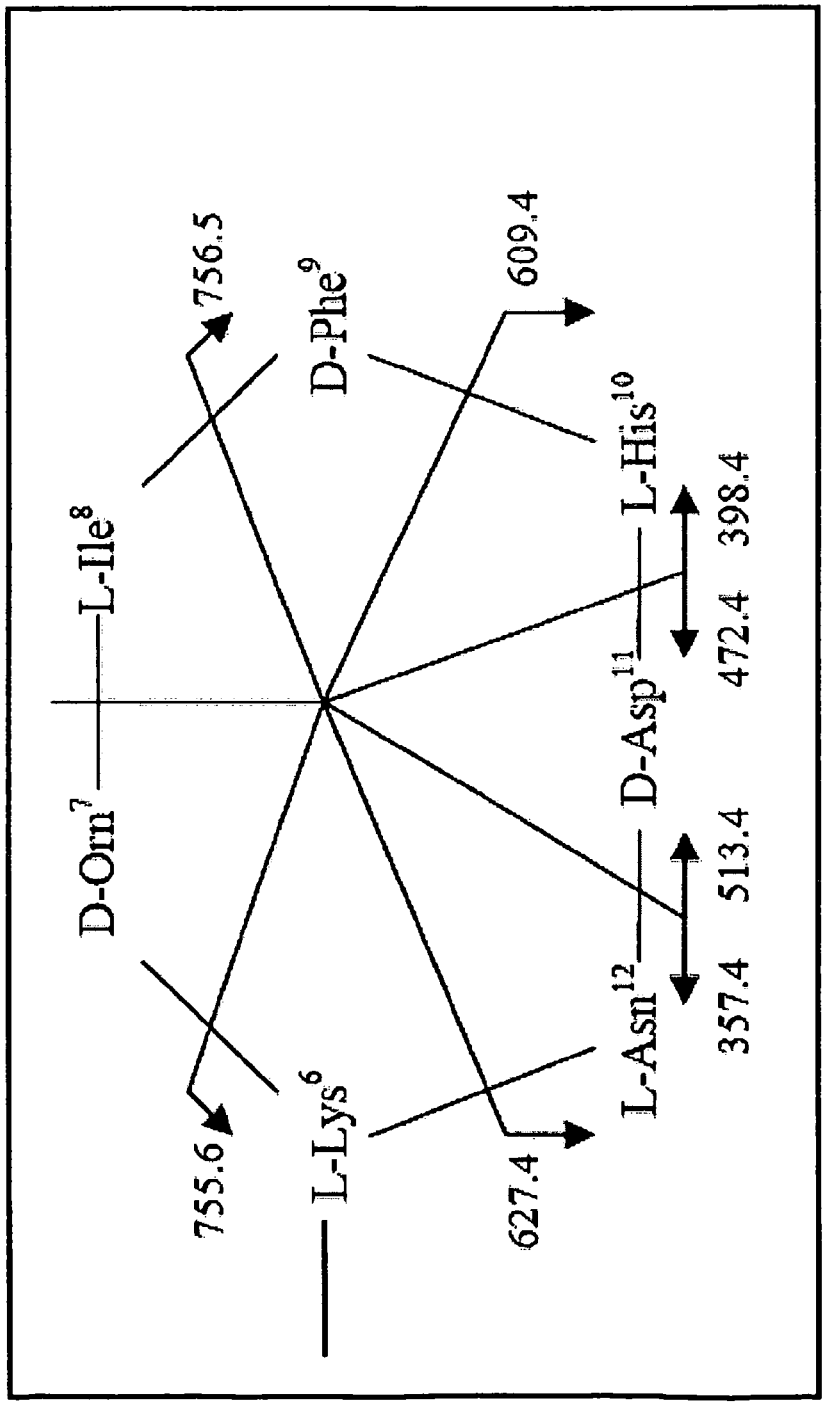
FIG. 3A shows the structure of the cyclic part of Bacitracin A, where fragment ion assignments are done for characteristic ions in the second-generation product ion spectrum below.
Figure 3B:
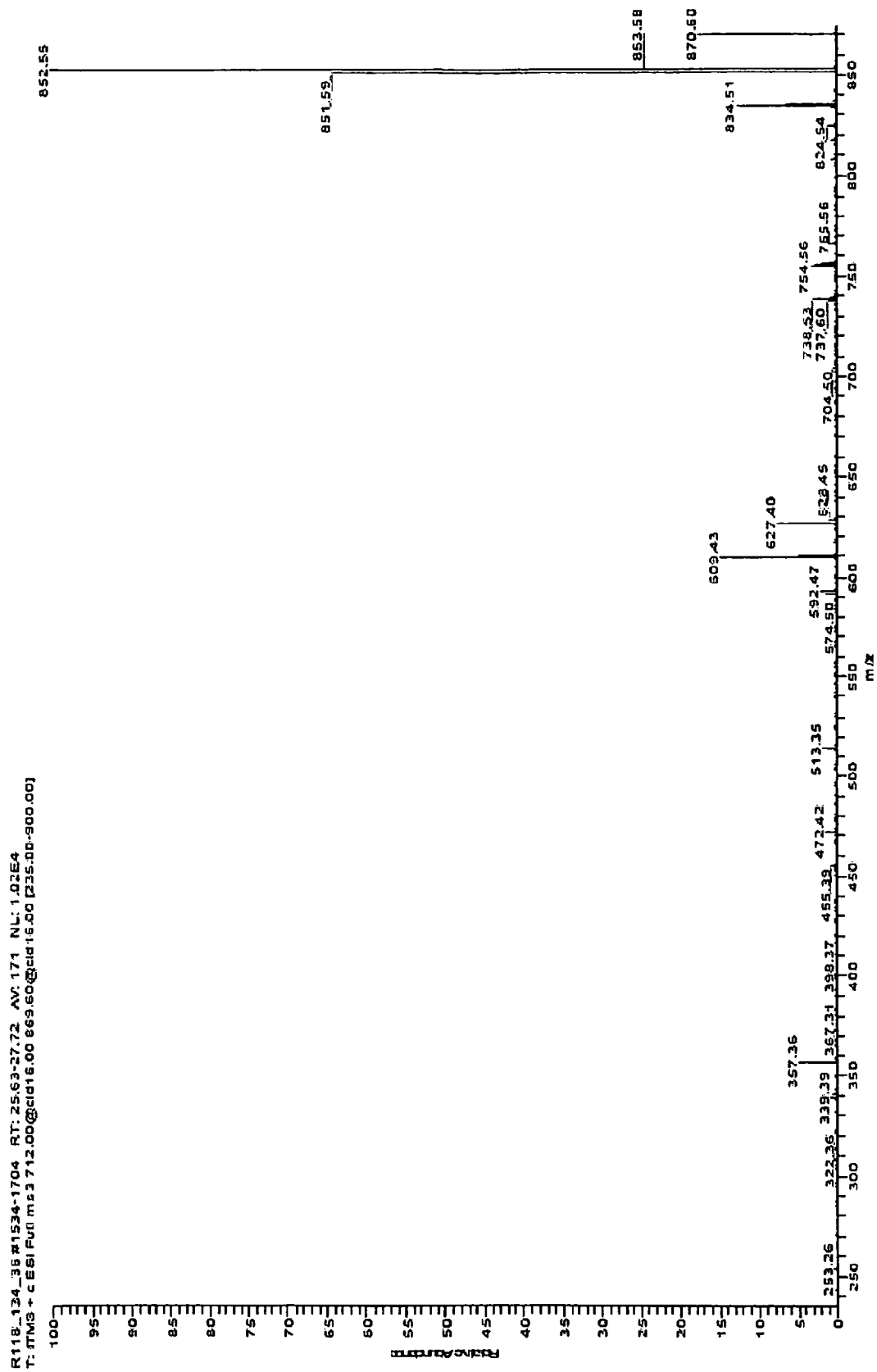
FIG. 3B shows the second-generation product ion (MS$^3$) spectrum of Bacitracin A, where the consecutive precursor ions were m/z 712.0 ([M+2H]$^{2+}$) and m/z 869.6 ([M+H]$^+$).

Sequencing of the cyclic part of Bacitracin A was performed by further isolating and fragmenting the ring part fragment ion at m/z 869.6 in a MS$^3$ experiment (712.0→869.6), see FIG. 3B. The preferential ring opening between Orn and Ile results in two series of fragment ions shown in FIG. 3A. One series comprises the product ions at m/z 756.5 (loss of Ile), m/z 609.4 (loss of IlePhe), m/z 472.4 (loss of IlePheHis) and at m/z 357.4 (loss of IlePheHisAsp). In the other series, product ions at m/z 755.6 (loss of Orn), m/z 627.4 (loss of OrnLys), m/z 513.4 (loss of OrnLysAsn) and at m/z 398.4 (loss of OrnLysAsnAsp) are found. All these fragment ions thus confirms the well-established sequence of Bacitracin A and presents a possibility to elucidate the sequence of unknown Bacitracin analogues by fragmentation pattern comparisons.

Bacitracin J1

Figure 4A:
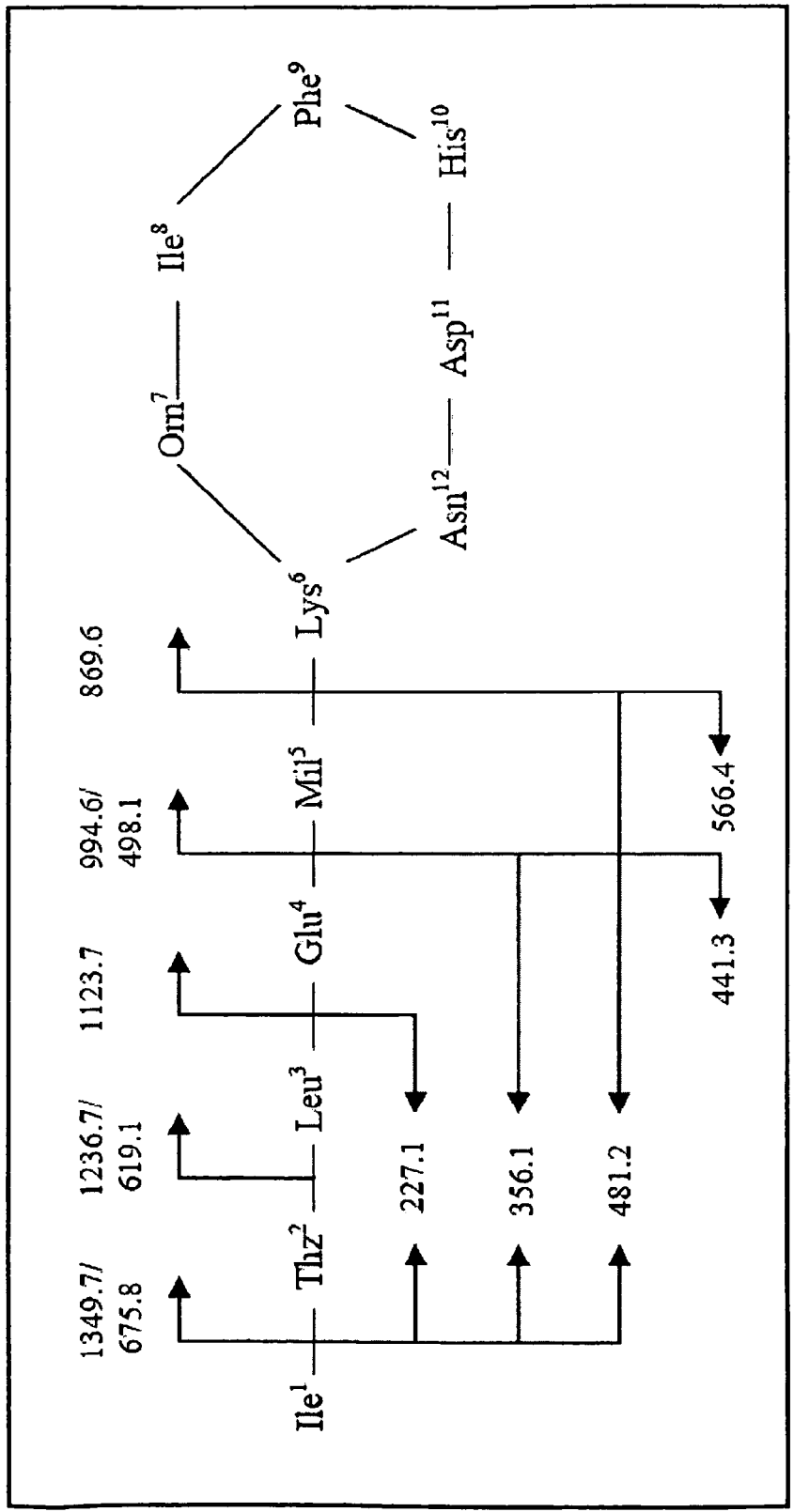
FIG. 4A shows the structure of Bacitracin J1, where fragment ion assignments are done for characteristic ions in the product ion spectrum below.
Figure 4B:
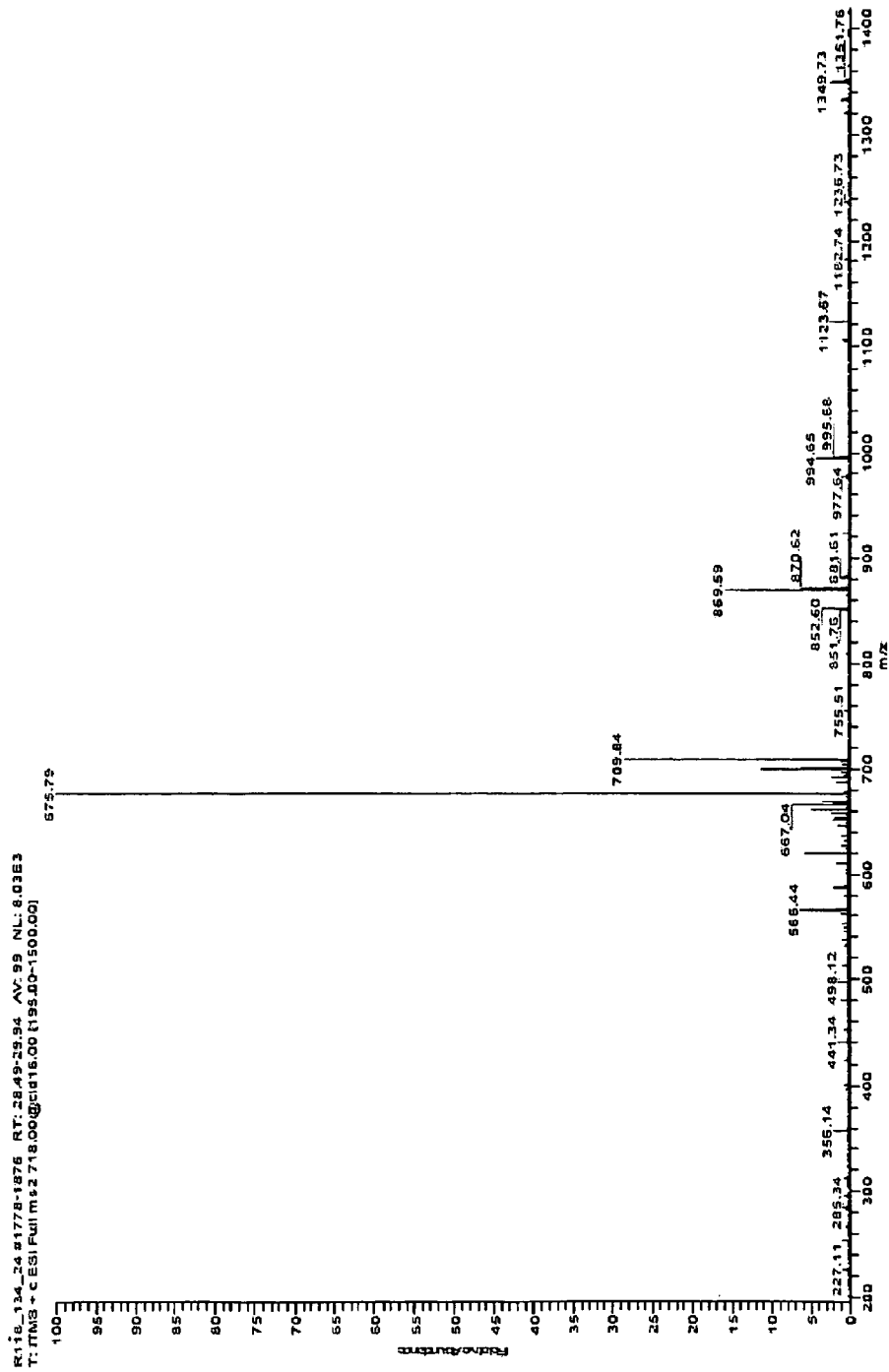
FIG. 4B shows the product ion (MS/MS) spectrum of Bacitracin J1, where the precursor ion at m/z 718.0 ([M+2H]$^2$) was isolated and fragmented.

Using the same methodology as for Bacitracin A, the location of a modification responsible for the +12 Da difference from Bacitracin A, could be determined. The doubly protonated molecular ion ([M+2H]$^{2+}$, m/z 718.0) was isolated and fragmented and the resulting product ion (MS/MS) spectrum is shown in FIG. 4B. The spectrum contains a full set of y″ ions with m/z 1349.7/675.8$^{2+}$ (loss of Ile), m/z 1236.7/ 619.1$^{2+}$ (loss of IleThz), m/z 1123.7 (loss of IleThzLeu), m/z 994.6/498.1$^{2+}$ (loss of IleThzLeuGlu) and m/z 869.6 (loss of IleThzLeuGluMil). These fragment assignments are visualized in FIG. 4A. In addition to the b ions with m/z 566.4 (IleThzLeuGluMil) and m/z 441.3 (IleThzLeuGlu), fragment ions resulting from pairs of bond cleavages can be seen at m/z 227.1 (ThzLeu), m/z 356.1 (ThzLeuGlu) and at m/z 481.2 (ThzLeuGluMil).

An LC-MS$^3$ experiment (718.0→869.6) gave the same characteristic fragment ions as for the corresponding experiment on the cyclic part of Bacitracin A. All these fragment ions are thus consistent with a residue weighing 12 Da more than Ile at position 5 in this component, while the rest of the sequence seems to be identical to Bacitracin A:s.

Bacitracin J2

Figure 5A:
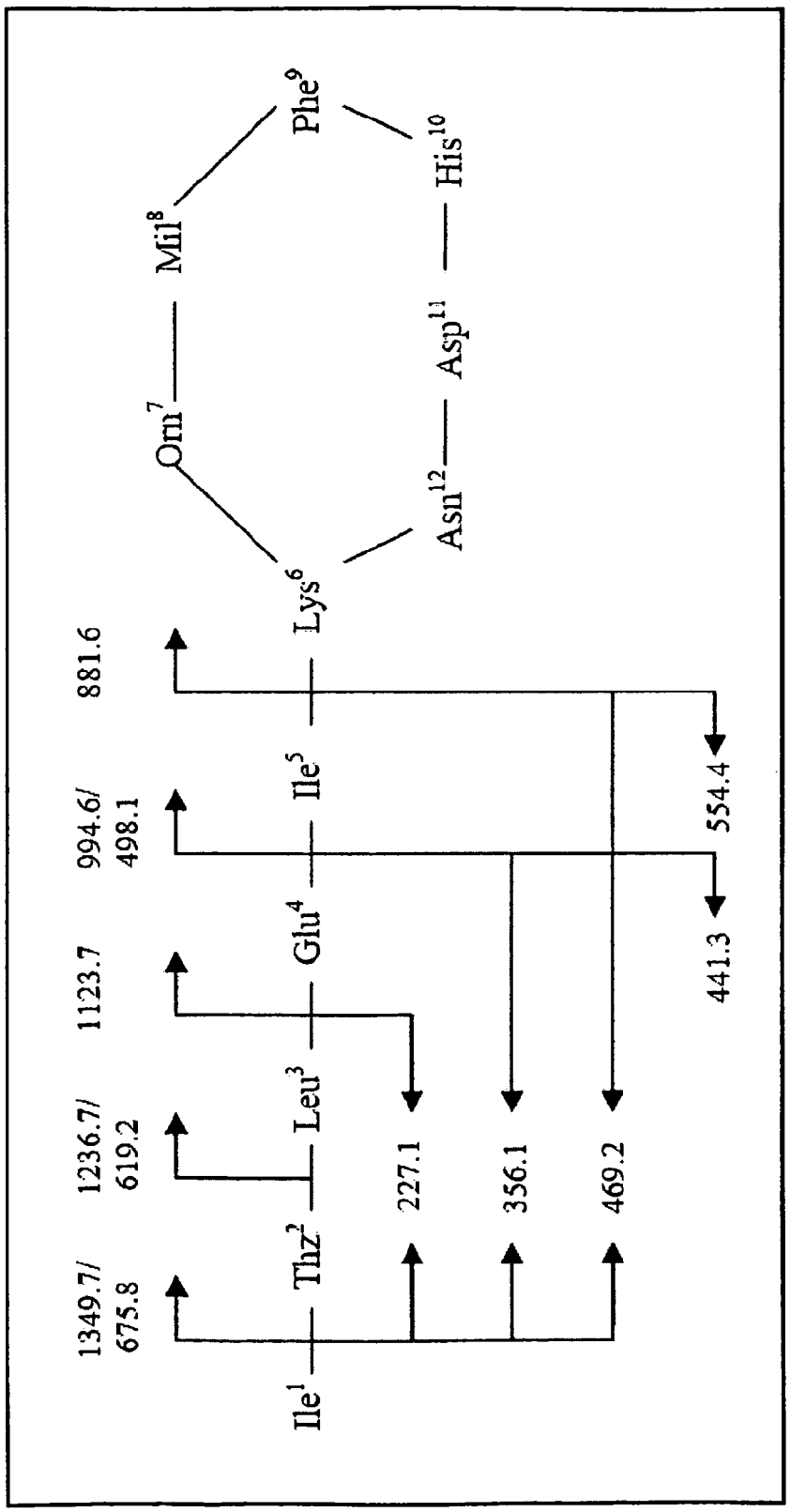
FIG. 5A shows the structure of Bacitracin J2, where fragment ion assignments are done for characteristic ions in the product ion spectrum below.
Figure 5B:
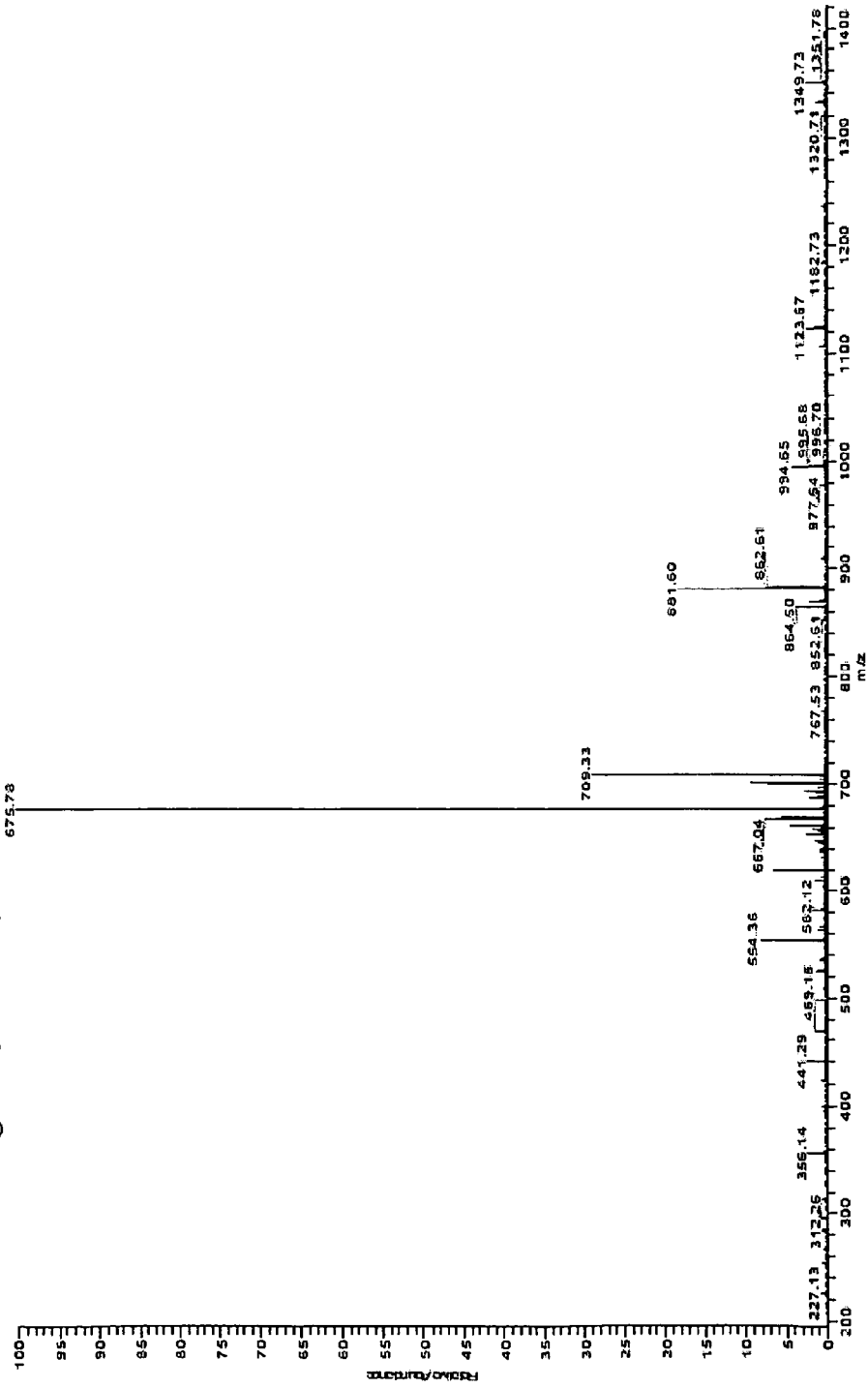
FIG. 5B shows the product ion (MS/MS) spectrum of Bacitracin J2, where the precursor ion at m/z 718.0 ([M+2H]$^{2+}$) was isolated and fragmented.

Using the same methodology as for Bacitracin A, the location of a modification responsible for the +12 Da difference from Bacitracin A, could be determined. The doubly protonated molecular ion ([M+2H]$^{2+}$, m/z 718.0) was isolated and fragmented and the resulting product ion (MS/MS) spectrum is shown in FIG. 5B.

The spectrum contains a full set of y" ions with m/z 1349.7/675.8$^{2+}$ (loss of Ile), m/z 1236.7/619.2$^{2+}$ (loss of IleThz), m/z 1123.7 (loss of IleThzLeu), m/z 994.6/498.1$^{2+}$ (loss of IleThzLeuGlu) and m/z 881.6 (loss of IleThzLeuGluIle). These fragment assignments are visualized in FIG. 5A. In addition to the b ions with m/z 554.4 (IleThzLeuGluIle) and m/z 441.3 (IleThzLeuGlu), fragment ions resulting from pairs of bond cleavages can be seen at m/z 227.1 (ThzLeu), m/z 356.1 (ThzLeuGlu) and at m/z 469.2 (ThzLeuGluIle). From these fragments it is obvious that the +12 Da modification from Bacitracin A is located in the ring portion of the molecule.

Figure 6A:
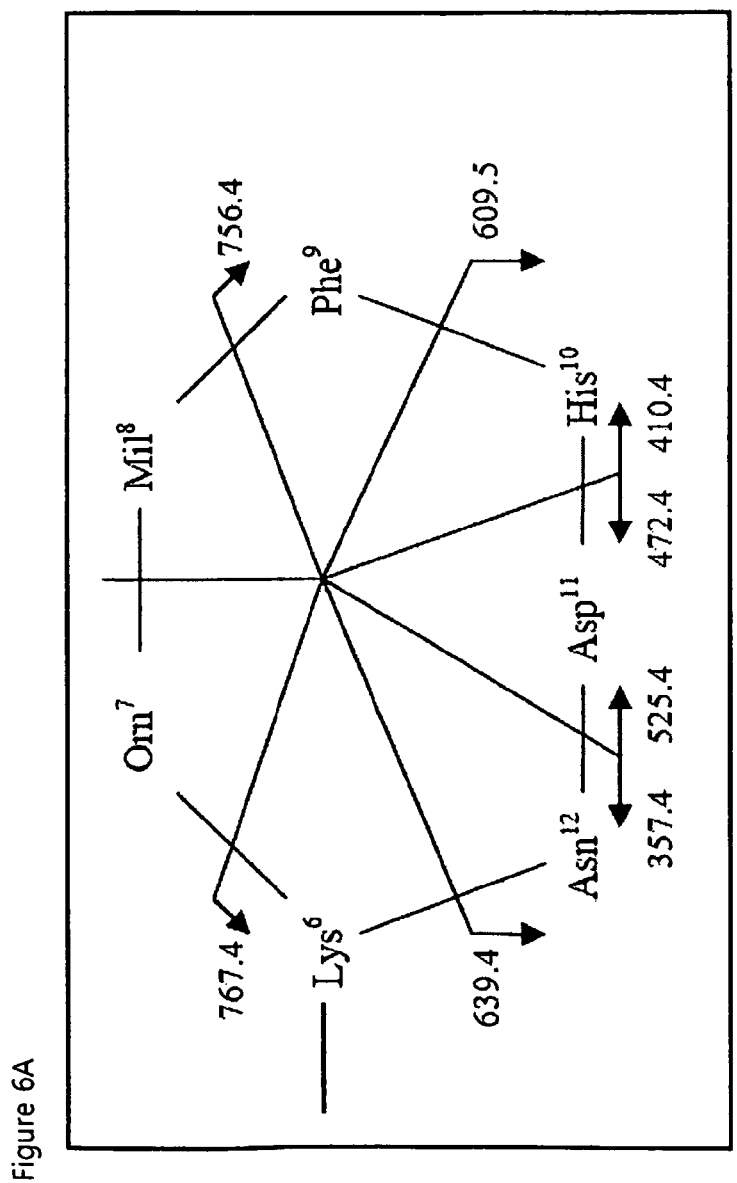
FIG. 6A shows the structure of the cyclic part of Bacitracin J2, where fragment ion assignments are done for characteristic ions in the second-generation product ion spectrum below.
Figure 6B:
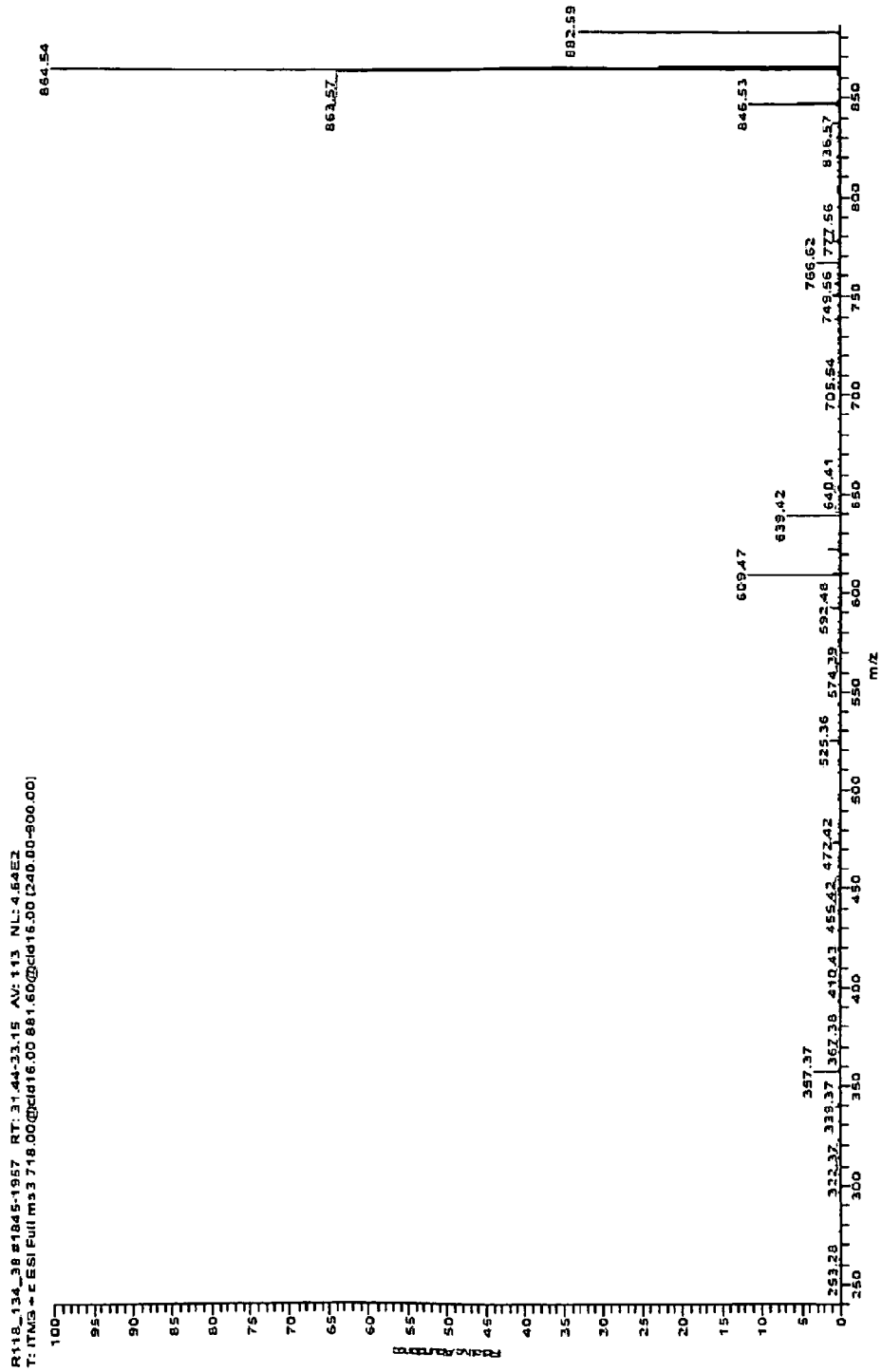
FIG. 6B shows the second-generation product ion (MS$^3$) spectrum of Bacitracin J2, where the consecutive precursor ions were m/z 718.0 ([M+2H]$^{2+}$) and m/z 881.6 ([M−H]$^+$).

Sequencing of the cyclic part of Bacitracin J2 was performed by further isolating and fragmenting the ring part fragment ion at m/z 881.6 in a MS$^3$ experiment (718.0→881.6), see FIG. 6B. The preferential ring opening between Orn and Ile results in two series of fragment ions shown in FIG. 6A. One series comprises the product ions at m/z 756.4 (loss of MiI), m/z 609.5 (loss of MilPhe), m/z 472.4 (loss of MilPheHis) and at m/z 357.4 (loss of MilPheHisAsp). In the other series, product ions at m/z 767.4 (loss of Orn), m/z 639.4 (loss of OrnLys), m/z 525.4 (loss of OrnLysAsn) and at m/z 410.4 (loss of OrnLysAsnAsp) are found. All these fragment ions are thus consistent with a residue weighing 12 Da more than Ile at position 8 in this component, while the rest of the sequence seems to be identical to Bacitracin A.

Bacitracin J3

Figure 7A:
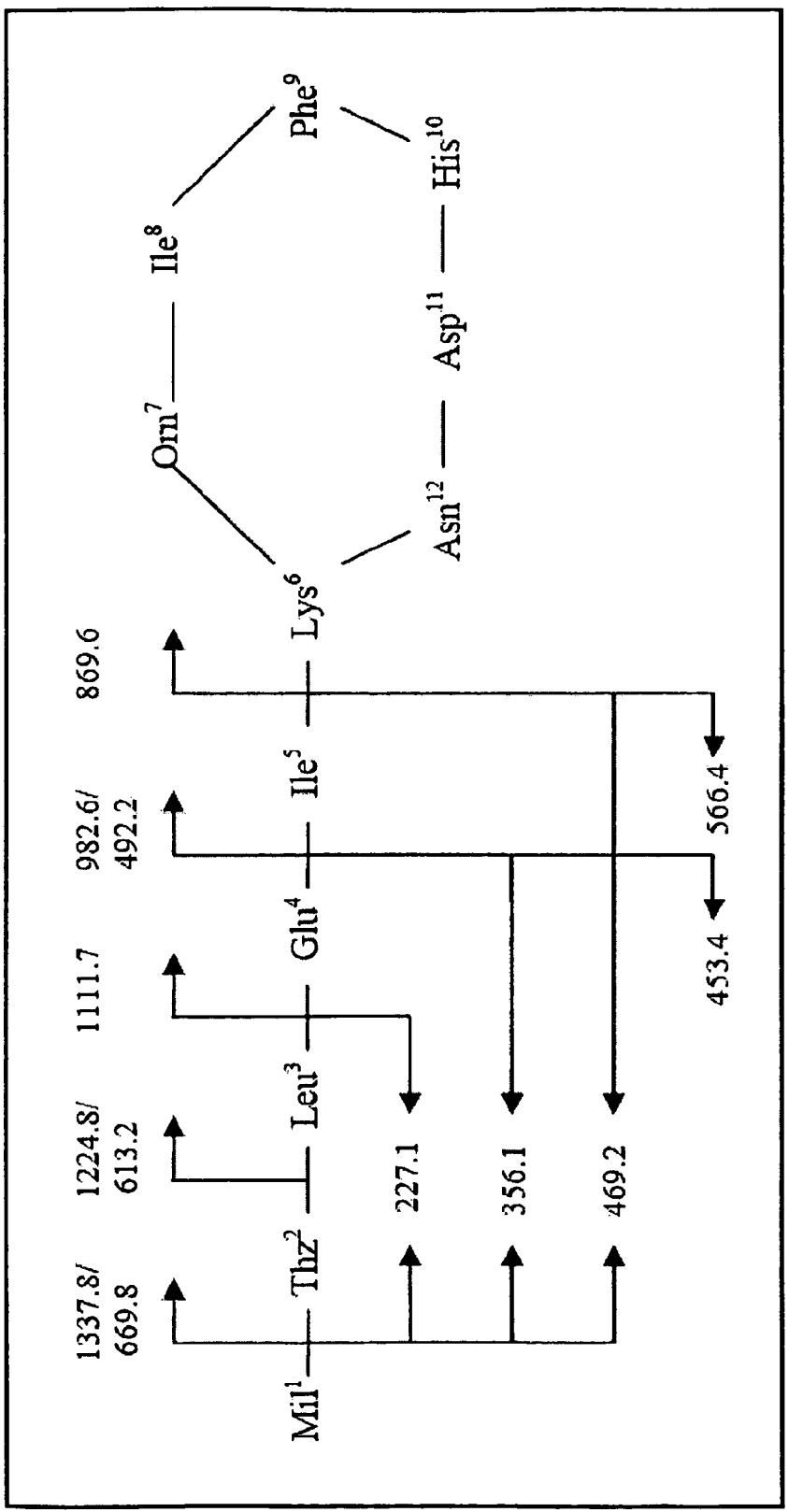
FIG. 7A shows the structure of Bacitracin J3, where fragment ion assignments are done for characteristic ions in the product ion spectrum below.
Figure 7B:
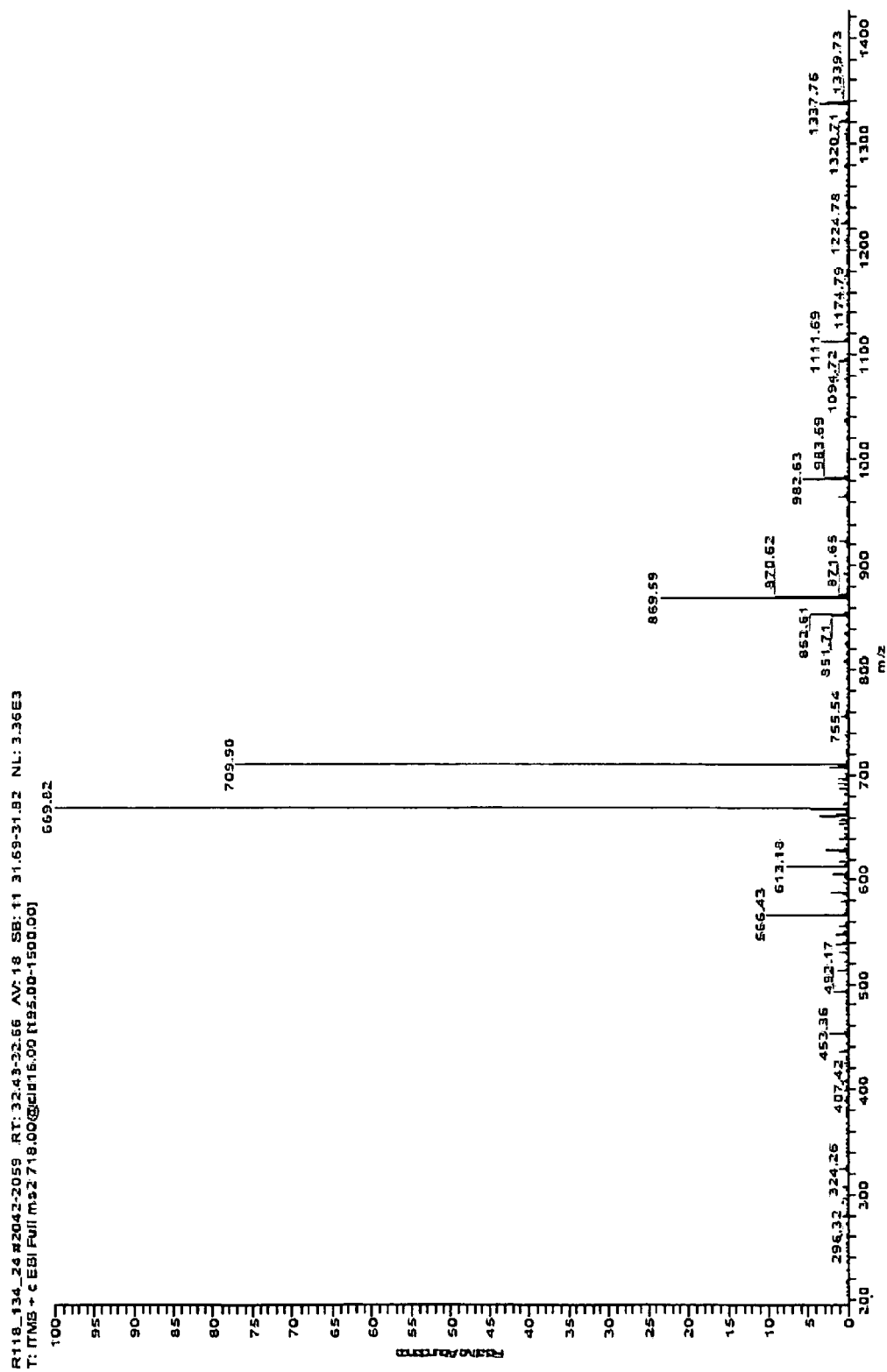
FIG. 7B shows the product ion (MS/MS) spectrum of Bacitracin J3, where the precursor ion at m/z 718.0 ([M+2H]$^{2+}$) was isolated and fragmented.
Figure 8A:
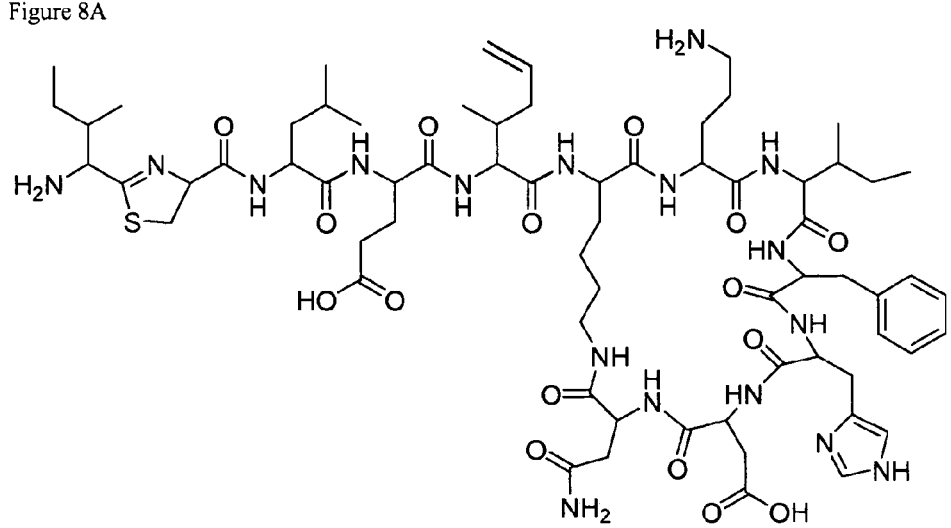
FIG. 8A shows the structure of Bacitracin with a 5-Methylene-Isoleucine residue in position 5 (=Bacitracin J1)
Figure 8B:
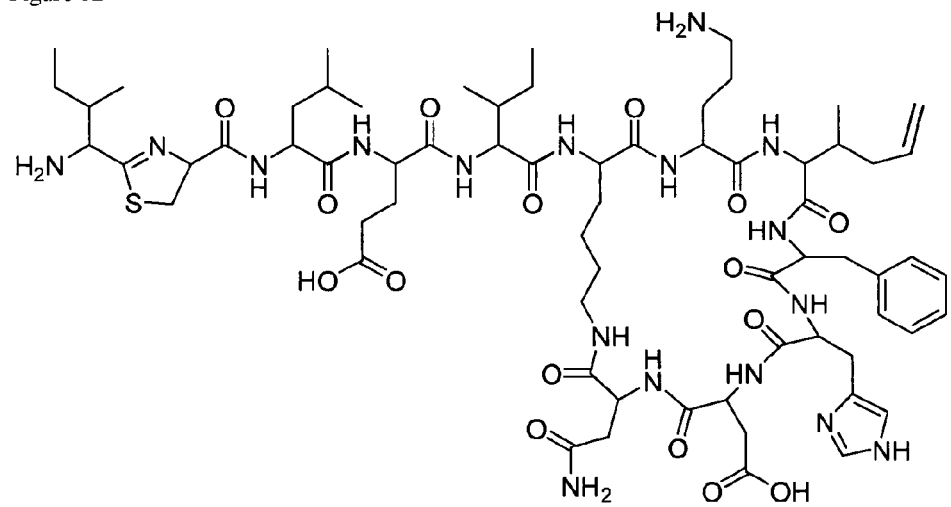
FIG. 8B shows the structure of Bacitracin with a 5-Methylene-Isoleucine residue in position 8 (=Bacitracin J2)
Figure 8C:
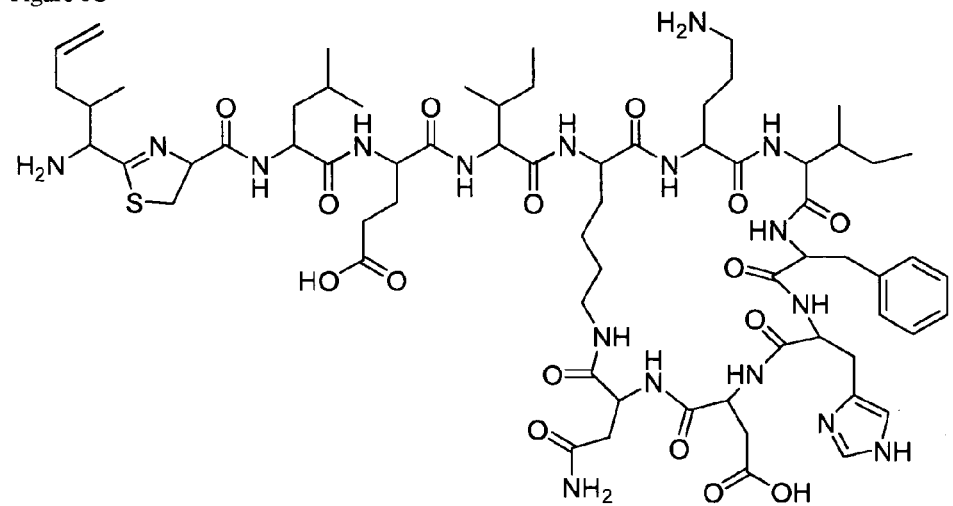
FIG. 8C shows the structure of Bacitracin with a 5-Methylene-Isoleucine residue in position 1 (=Bacitracin J3)
Figure 8D:
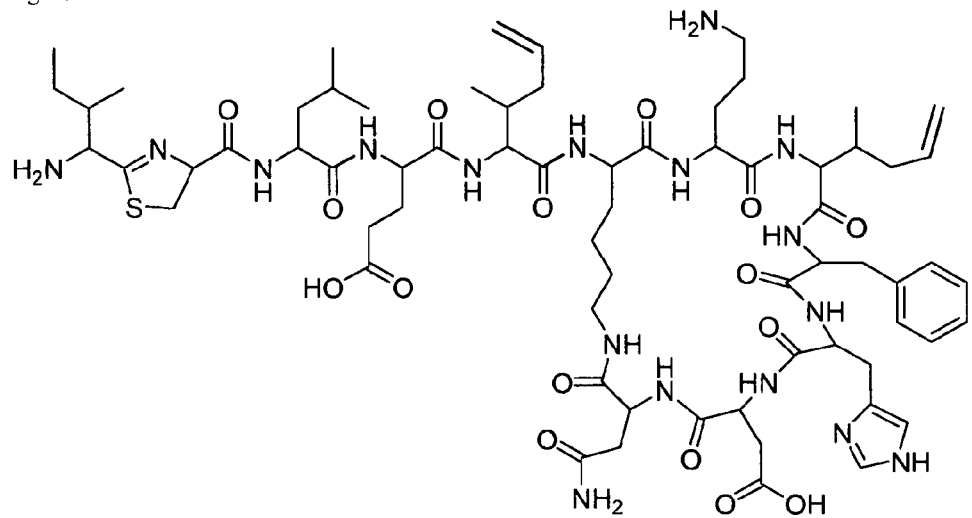
FIG. 8D shows the structure of Bacitracin with 5-Methylene-Isoleucine residues in position 5 and 8 (=Bacitracin K1)
Figure 8E:
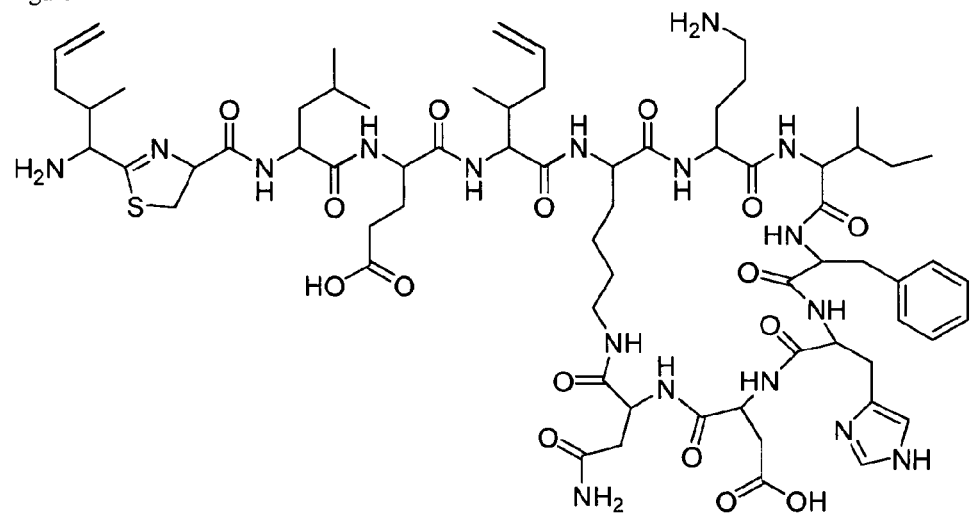
FIG. 8E shows the structure of Bacitracin with 5-Methylene-Isoleucine residues in position 1 and 5 (=Bacitracin K2)
Figure 8F:
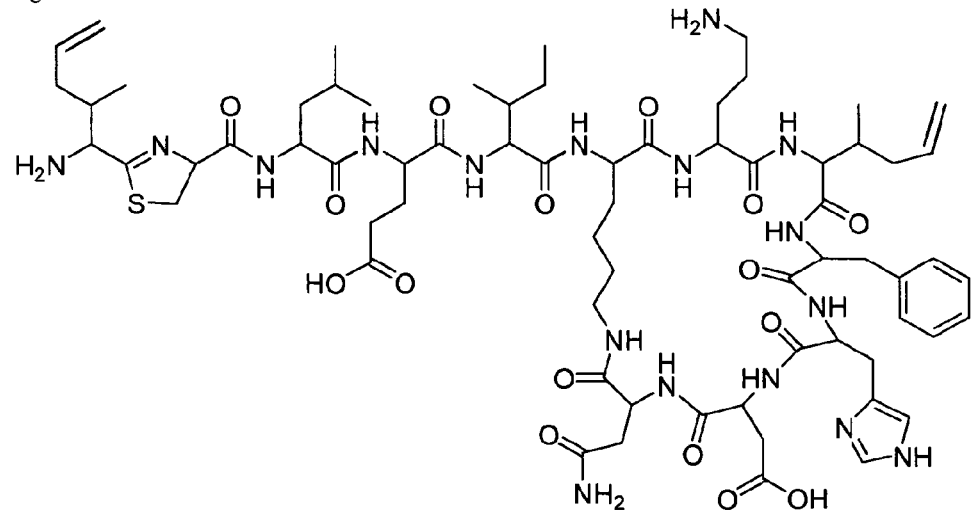
FIG. 8F shows the structure of Bacitracin with 5-Methylene-Isoleucine residues in position 1 and 8 (=Bacitracin K3)
Figure 8G:
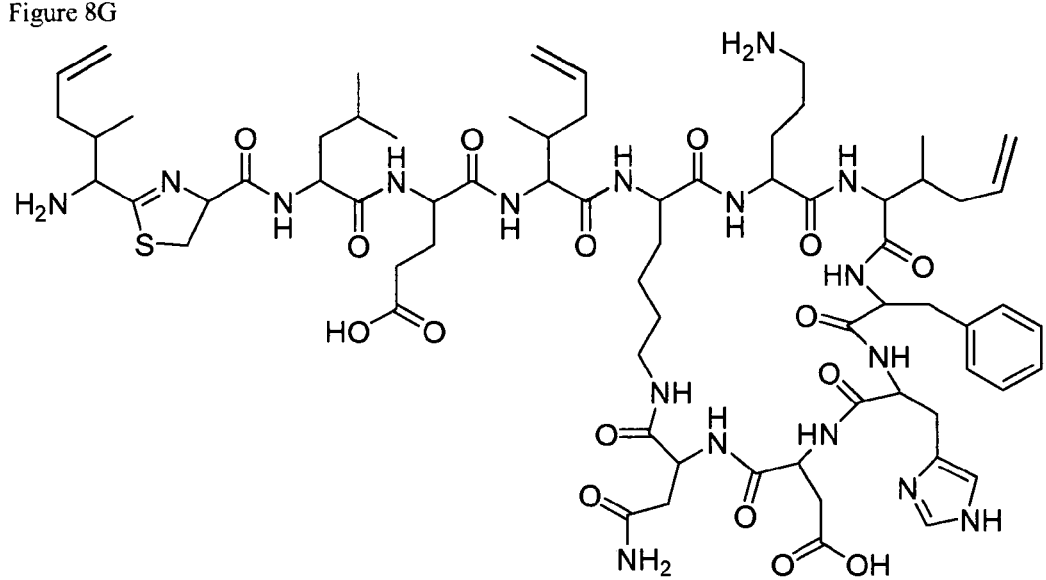
FIG. 8G shows the structure of Bacitracin with 5-Methylene-Isoleucine residues in position 1, 5 and 8 (=Bacitracin L)

Using the same methodology as for Bacitracin A, the location of a modification responsible for the +12 Da difference from Bacitracin A, could be determined. The doubly protonated molecular ion ([M+2H]$^{2+}$, m/z 718.0) was isolated and fragmented and the resulting product ion (MS/MS) spectrum is shown in FIG. 7B.

The spectrum contains a full set of y" ions with m/z 1337.8/669.8$^{2+}$ (loss of MiI), m/z 1224.8/613.2$^{2+}$ (loss of (MilThz), m/z 1111.7 (loss of MilThzLeu), m/z 982.6/492.2$^{2+}$ (loss of MilThzLeuGlu) and m/z 869.6 (loss of MilThzLeuGluIle). These fragment assignments are visualized in FIG. 7A. In addition to the b ions with m/z 566.4 (MilThzLeuGluIle) and m/z 453.4 (MilThzLeuGlu), fragment ions resulting from pairs of bond cleavages can be seen at m/z 227.1 (ThzLeu), m/z 356.1 (ThzLeuGlu) and at m/z 469.2 (ThzLeuGluIle).

An LC-MS$^3$ experiment (718.0→869.6) gave the same characteristic fragment ions as for the corresponding experiment on the cyclic part of Bacitracin A. All these fragment ions are thus consistent with a residue weighing 12 Da more than Ile at position 1 in this component, while the rest of the sequence seems to be identical to Bacitracin A:s.

Experiment 2

Isolating the Components

In order to elucidate the structures of the three components with NMR spectroscopy, enriched samples had to be prepared. Ideally, each of the three components should be isolated to about 90% purity to obtain "clean" NMR spectra, free from interfering signals from other components. The isolation was done in two steps. In the first step, a LiChroprep RP-18-column (25-40 µm, 35×5 cm) was used to remove the components eluting before and after the three components. The mobile phase consisted of methanol/acetonitrile/0.03 M ammonium formate pH 6.0 3.5:31.5:65, v/v/v. In this way, purified material with a total purity of about 25% for the three components was obtained. In the second step, an YMC-Pack ODS-A-column (5 µm, 250×10 mm) was used to separate the three components from each other. The mobile phase consisted of methanol/acetonitrile/0.025 M ammonium acetate pH 6.0 58:5:37, v/v/v. The final result of this 2-step purification were 4 samples (denoted samples B, B', C and C'), where samples B and B' were similar and contained mainly Bacitracin J1 and Bacitracin A, and where samples C and C' were similar and contained mainly Bacitracin J2 and Bacitracin J3 (Table 1). LC-MS" was performed on all samples in order to verify that the right components had been isolated. The purity of samples B and C was much lower than what usually is thought to be necessary for full NMR elucidation. However, as the other main component in sample B was Bacitracin A, it was decided to try an NMR investigation without further purification. By first performing NMR investigation on a sample with enriched content of Bacitracin A (denoted sample A, earlier prepared), it was hoped that in addition to serve as a reference compound, the signals from Bacitracin A could be omitted from the spectra of sample B. As sample C contained a mixture of Bacitracin J2 and Bacitracin J3, full structural elucidation could not be expected due to an anticipated high degree of overlapping signals. However, as the modifications in these components were expected to be the same as in Bacitracin J1 (from LC-MS' trials, see Experiment 1), it was still hoped that the NMR experiments in combination with the results from LC-MS", would give sufficient structural evidence.

TABLE 1

The proportions (area-% at 254 nm) of the components Bacitracin A, Bacitracin J1, Bacitracin J2 and Bacitracin J3 in samples A, B, B', C and C'.

| Sample | Bacitracin A area-% | Bacitracin J1 area-% | Bacitracin J2 area-% | Bacitracin J3 area-% |
|---|---|---|---|---|
| A | 93 | — | — | — |
| B | 20 | 63 | — | — |
| B' | 12 | 54 | 4 | 2 |
| C | 4 | 2 | 54 | 20 |
| C' | — | 3 | 52 | 20 |

Experiment 3

Accurate Mass Determination

Samples A, B' and C were analyzed by accurate mass determination (see Table 2). The molecular weight difference between Bacitracin J1/Bacitracin A was 11.9998. The molecular weight differences between both Bacitracin J2/Bacitracin A and Bacitracin J3/Bacitracin A were 12.0000, respectively. This gave further evidence that the components Bacitracin J1, Bacitracin J2 and Bacitracin J3 had elemental compositions consisting of one more carbon atom (exact mass 12.0000) than Bacitracin A.

TABLE 2

Exact mass obtained by accurate mass determinations on samples A, B' and C.

| Sample | Bacitracin A Exact mass | Bacitracin J1 Exact mass | Bacitracin J2 and Bacitracin J3 Exact mass |
|---|---|---|---|
| A | 1421.7560 | | |
| B' | | 1433.7558 | |
| C | | | 1433.7560 |

Experiment 4

NMR

NMR spectra were recorded on 10 mM solutions of samples A, B and C in 95% phosphate buffer pH 6.5/5% $D_2O$ at 303 K. The experiments were obtained on a Bruker 600 MHz spectrometer using standard pulse sequences for two-dimensional homonuclear proton chemical shift correlation (DQF-COSY, TOCSY, NOESY), heteronuclear $^1H$—$^{13}C$ correlation (HSQC, HMBC) and heteronuclear $^1H$—$^{15}N$ correlation (HSQC) experiments. Mixing times of 20 ms and 60 ms were used for TOCSY experiments and mixing times of 100 ms, 200 ms, 400 ms and 600 ms were used in the NOESY experiments. For sample C, a DEPT(135) experiment was obtained. Chemical shifts are reported in p.p.m., using internal 2,2-Dimethyl-2-silapentane-5-sulfonic acid (0.5 mM) as reference.

Results

Sample A (Bacitracin A)

Identification of the amino acid spin-systems were done by 2D $^1H$—$^1H$ chemical shift correlation experiments (DQF-COSY and TOCSY) and heteronuclear $^1H$—$^{13}C$ and $^1H$—$^{15}N$ chemical shift correlation (HSQC) in the $^1H$ detected mode and the data are summarized in Table 3. The chemical shift data are consistent with the presence of residues Ile, Thz, Leu, Glu, Ile, Lys, Orn, Ile, Phe, His, Asp and Asn both from comparisons of $^1H$ chemical shift data in Kobayashi et al. (1992) (see Table 3) and chemical shift statistics found in the BMRB database (see Table 3).

The sequence of the amino acid residues was established from 2D $^1H$—$^1H$ (NOESY, Table 4) and $^1H$—$^{13}C$ (HMBC, Table 5) correlation experiments. The dipolar coupling (through space, NOESY) and long-range scalar coupling (HMBC) were in accordance with the well-established sequence of Bacitracin A:

Structure 1: Bacitracin A.

Ile$^1$-Thz$^2$-Leu$^3$-Glu$^4$-Ile$^5$-Lys$^6$-Orn$^7$-Ile$^8$-Phe$^9$-His$^{10}$-Asp$^{11}$-Asn$^{12}$

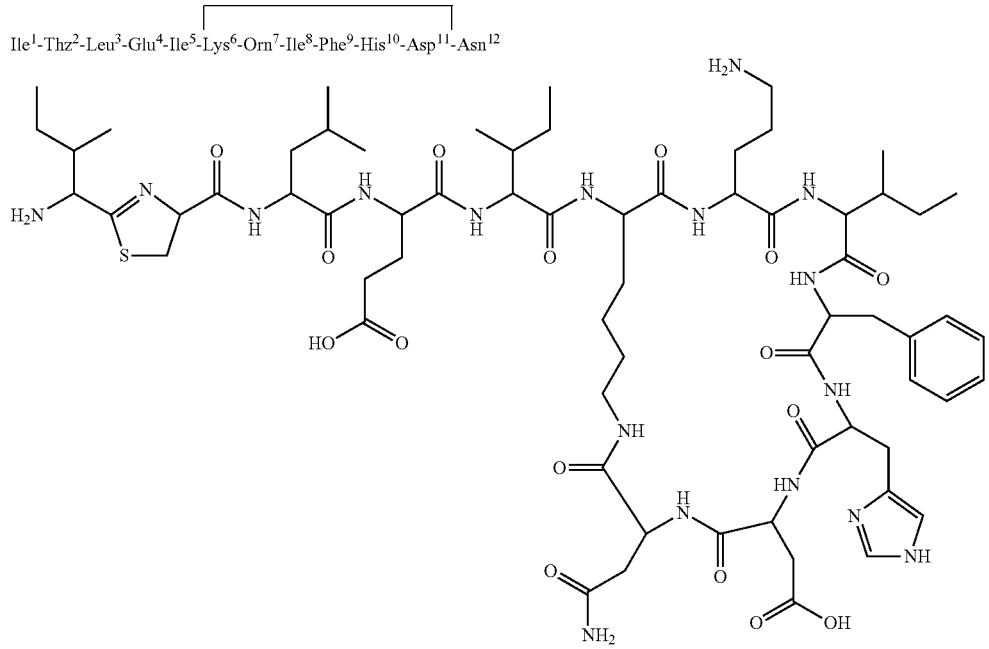

TABLE 3

$^1H$, $^{13}C$ and $^{15}N$ chemical shifts for Bacitracin A (in sample A) and Bacitracin J1 (in sample B). Data was recorded in 95% phosphate buffer pH 6.5/5% $D_2O$ at 303K. Chemical shifts are reported in p.p.m., using internal 2,2-Dimethyl-2-silapentane-5-sulfonic acid (0.5 mM) as reference.

| Residue | Atom name [a] | Bacitracin A shift observed | Bacitracin J1 shift observed | Bacitracin A shift from publication [b] | Chemical shift statistics [c] |
|---|---|---|---|---|---|
| Ile$^1$ | H | — | — | — | 8.28 |
| | HA | 4.30 | 4.31 | 4.35 | 4.18 |
| | HB | 2.08 | 2.09 | 2.09 | 1.79 |
| | HG12 | 1.50 | 1.50 | 1.50 | 1.27 |
| | HG13 | 1.28 | 1.28 | 1.31 | 1.21 |
| | HG2 | 1.05 | 1.06 | 1.07 | 0.78 |
| | HD1 | 0.95 | 0.96 | 0.97 | 0.68 |
| | C | 175.2 | 175.1 | — | 175.89 |

TABLE 3-continued $^1$H, $^{13}$C and $^{15}$N chemical shifts for Bacitracin A (in sample A) and Bacitracin J1 (in sample B). Data was recorded in 95% phosphate buffer pH 6.5/5% D$_2$O at 303K. Chemical shifts are reported in p.p.m., using internal 2,2-Dimethyl-2-silapentane-5-sulfonic acid (0.5 mM) as reference.

| Residue | Atom name [a] | Bacitracin A shift observed | Bacitracin J1 shift observed | Bacitracin A shift from publication [b] | Chemical shift statistics [c] |
|---|---|---|---|---|---|
| | CA | 60.2 | 60.2 | — | 61.63 |
| | CB | 39.7 | 39.6 | — | 38.61 |
| | CG1 | 26.6 | 26.7 | — | 27.74 |
| | CG2 | 17.0 | 16.9 | — | 17.54 |
| | CD1 | 13.6 | 13.6 | — | 13.46 |
| | N | — | — | — | 121.51 |
| Thz[2] | H | — | — | — | |
| | HA | 5.25 | 5.24 | 5.28 | |
| | HB2 | 3.79 | 3.79 | 3.79 | |
| | HB3 | 3.60 | 3.61 | 3.59 | |
| | HG | — | — | — | |
| | C | 175.6 | 175.5 | — | |
| | CA | 79.9 | 79.9 | — | |
| | CB | 38.6 | 38.6 | — | |
| | N | — | — | — | |
| Leu[3] | H | 8.19 | 8.20 | 8.16 | 8.22 |
| | HA | 4.44 | 4.44 | 4.52 | 4.31 |
| | HB2 | 1.69 | 1.70 | 1.61 | 1.62 |
| | HB3 | 1.60 | 1.60 | 1.61 | 1.54 |
| | HG | 1.58 | 1.59 | 1.71 | 1.51 |
| | HD1 | 0.92 | 0.92 | 0.94 | 0.76 |
| | HD2 | 0.86 | 0.88 | 0.89 | 0.74 |
| | C | 177.5 | 177.6 | — | 177.01 |
| | CA | 55.4 | 55.5 | — | 55.66 |
| | CB | 42.9 | 42.8 | — | 42.29 |
| | CG | 27.1 | 27.0 | — | 26.80 |
| | CD1 | 24.8 | 24.9 | — | 24.68 |
| | CD2 | 23.5 | 23.5 | — | 24.10 |
| | N | 124.1 | 124.2 | — | 121.85 |
| Glu[4] | H | 8.82 | 8.84 | 8.67 | 8.33 |
| | HA | 4.26 | 4.26 | 4.43 | 4.25 |
| | HB2 | 2.06 | 2.08 | 2.16 | 2.03 |
| | HB3 | 1.94 | 1.94 | 2.01 | 2.00 |
| | HG2 | 2.27 | 2.28 | 2.46 | 2.28 |
| | HG3 | 2.27 | 2.28 | 2.46 | 2.26 |
| | C | 176.7 | 176.5 | — | 176.93 |
| | CA | 57.1 | 56.9 | — | 57.36 |
| | CB | 30.1 | 30.1 | — | 30.00 |
| | CG | 36.2 | 36.1 | — | 36.09 |
| | CD | 183.8 | 183.6 | — | 182.57 |
| | N | 121.4 | 121.4 | — | 120.68 |
| Ile[5] | H | 8.16 | — | 8.07 | 8.28 |
| | HA | 4.12 | — | 4.16 | 4.18 |
| | HB | 1.82 | — | 1.65 | 1.79 |
| | HG12 | 1.37 | — | 1.39 | 1.27 |
| | HG13 | 1.12 | — | 1.14 | 1.21 |
| | HG2 | 0.82 | — | 0.85 | 0.78 |
| | HD1 | 0.81 | — | 0.83 | 0.68 |
| | C | 176.0 | — | — | 175.89 |
| | CA | 61.2 | — | — | 61.63 |
| | CB | 38.5 | — | — | 38.61 |
| | CG1 | 27.1 | — | — | 27.74 |
| | CG2 | 17.4 | — | — | 17.54 |
| | CD1 | 12.9 | — | — | 13.46 |
| | N | 120.2 | — | — | 121.51 |
| Lys[6] | H | 8.31 | 8.33 | 8.29 | 8.19 |
| | HA | 4.26 | 4.27 | 4.31 | 4.26 |
| | HB2 | 1.81 | 1.81 | 1.82 | 1.78 |
| | HB3 | 1.71 | 1.70 | 1.82 | 1.75 |
| | HG2 | 1.38 | 1.39 | 1.34 | 1.37 |
| | HG3 | 1.29 | 1.29 | 1.33 | 1.36 |
| | HD2 | 1.51 | 1.51 | 1.52 | 1.61 |
| | HD3 | 1.51 | 1.51 | 1.52 | 1.60 |
| | HE2 | 3.21 | 3.21 | 3.28 | 2.92 |
| | HE3 | 3.21 | 3.21 | 3.20 | 2.91 |
| | HZ | 8.04 | 8.04 | 7.83 | 7.42 |
| | C | 175.7 | 176.4 | — | 176.68 |
| | CA | 56.9 | 56.8 | — | 56.97 |
| | CB | 33.1 | 33.2 | — | 32.78 |
| | CG | 24.6 | 24.7 | — | 24.93 |
| | CD | 29.8 | 29.8 | — | 28.96 |
| | CE | 41.5 | 41.6 | — | 41.91 |
| | N | 121.0 | 121.1 | — | 121.07 |
| | NZ | 120.7 | 120.7 | — | 34.01 |
| Orn[7] | H | 8.18 | 8.23 | 8.11 | — |
| | HA | 4.44 | 4.44 | 4.48 | — |
| | HB2 | 1.87 | 1.87 | 1.70 | — |
| | HB3 | 1.78 | 1.77 | 1.70 | — |
| | HG2 | 1.67 | 1.68 | 1.86 | — |
| | HG3 | 1.67 | 1.68 | 1.77 | — |
| | HD2 | 3.01 | 3.01 | 3.04 | — |
| | HD3 | 3.01 | 3.01 | 3.04 | — |
| | HE | — | — | 7.58 | — |
| | C | 175.7 | 175.7 | — | — |
| | CA | 55.4 | 55.5 | — | — |
| | CB | 31.3 | 31.2 | — | — |
| | CG | 26.1 | 26.1 | — | — |
| | CD | 41.9 | 41.8 | — | — |
| | N | 119.9 | 120.0 | — | — |
| | NE | — | — | — | — |
| Ile[8] | H | 8.31 | 8.32 | 8.17 | 8.28 |
| | HA | 4.10 | 4.09 | 4.17 | 4.18 |
| | HB | 1.70 | 1.69 | 1.72 | 1.79 |
| | HG12 | 1.20 | 1.21 | 1.22 | 1.27 |
| | HG13 | 0.96 | 0.97 | 0.99 | 1.21 |
| | HG2 | 0.56 | 0.56 | 0.60 | 0.78 |
| | HD1 | 0.75 | 0.75 | 0.76 | 0.68 |
| | C | 176.1 | 176.1 | — | 175.89 |
| | CA | 61.2 | 61.3 | — | 61.63 |
| | CB | 38.5 | 38.5 | — | 38.61 |
| | CG1 | 27.1 | 27.0 | — | 27.74 |
| | CG2 | 17.1 | 17.1 | — | 17.54 |
| | CD1 | 13.0 | 13.0 | — | 13.46 |
| | N | 124.7 | 125.0 | — | 121.51 |
| Phe[9] | H | 8.62 | 8.65 | 8.55 | 8.36 |
| | HA | 4.64 | 4.64 | 4.65 | 4.62 |
| | HB2 | 3.15 | 3.16 | 3.19 | 3.00 |
| | HB3 | 2.86 | 2.86 | 2.90 | 2.95 |
| | HD1 | 7.22 | 7.23 | 7.22 | 7.06 |
| | HD2 | 7.22 | 7.23 | 7.22 | 7.06 |
| | HE1 | 7.33 | 7.34 | 7.31 | 7.09 |
| | HE2 | 7.33 | 7.34 | 7.31 | 7.08 |
| | HZ | 7.28 | 7.28 | 7.26 | 7.01 |
| | C | 175.3 | 175.3 | — | 175.48 |
| | CA | 57.8 | 57.8 | — | 58.13 |
| | CB | 39.9 | 39.9 | — | 39.93 |
| | CG | 139.0 | 139.0 | — | 138.26 |
| | CD1 | 131.8 | 131.8 | — | 131.54 |
| | CD2 | 131.8 | 131.8 | — | 131.60 |
| | CE1 | 131.5 | 131.5 | — | 130.67 |
| | CE2 | 131.5 | 131.5 | — | 130.76 |
| | CZ | 129.9 | 129.9 | — | 129.23 |
| | N | 125.0 | 125.1 | — | 120.51 |
| His[10] | H | 8.54 | 8.55 | 8.59 | 8.23 |
| | HA | 4.81 | 4.82 | 4.82 | 4.61 |
| | HB2 | 3.20 | 3.22 | 3.30 | 3.11 |
| | HB3 | 2.96 | 2.97 | 3.03 | 3.05 |
| | HD1 | — | — | — | 8.85 |
| | HD2 | 6.97 | 6.99 | 8.55 | 7.03 |
| | HE1 | 8.45 | 8.55 | 7.03 | 7.98 |
| | HE2 | — | — | — | 9.82 |
| | C | 174.0 | 173.8 | — | 175.28 |
| | CA | 55.2 | 55.1 | — | 56.49 |
| | CB | 30.6 | 30.3 | — | 30.19 |
| | CG | 131.4 | 131.0 | — | 131.49 |
| | CD2 | 120.3 | 120.2 | — | 120.46 |
| | CE1 | 137.0 | 136.6 | — | 137.53 |
| | N | 119.8 | 119.6 | — | 119.56 |

TABLE 3-continued $^1$H, $^{13}$C and $^{15}$N chemical shifts for Bacitracin A (in sample A) and Bacitracin J1 (in sample B). Data was recorded in 95% phosphate buffer pH 6.5/5% D$_2$O at 303K. Chemical shifts are reported in p.p.m., using internal 2,2-Dimethyl-2-silapentane-5-sulfonic acid (0.5 mM) as reference.

| Residue | Atom name [a] | Bacitracin A shift observed | Bacitracin J1 shift observed | Bacitracin A shift from publication [b] | Chemical shift statistics [c] |
|---|---|---|---|---|---|
|  | ND1 | — | — | — | 195.69 |
|  | NE2 | — | — | — | 182.33 |
| Asp[11] | H | 8.66 | 8.69 | 8.75 | 8.31 |
|  | HA | 4.64 | 4.65 | 4.73 | 4.60 |
|  | HB2 | 2.66 | 2.68 | 2.87 | 2.72 |
|  | HB3 | 2.61 | 2.61 | 2.79 | 2.67 |
|  | C | 175.8 | 175.7 | — | 176.44 |
|  | CA | 54.5 | 54.4 | — | 54.68 |
|  | CB | 41.7 | 41.6 | — | 40.87 |
|  | CG | 180.0 | 180.0 | — | 179.27 |
|  | N | 121.5 | 121.4 | — | 120.69 |
| Asn[12] | H | 8.66 | 8.66 | 8.61 | 8.35 |
|  | HA | 4.64 | 4.64 | 4.70 | 4.67 |
|  | HB2 | 2.81 | 2.82 | 2.91 | 2.81 |
|  | HB3 | 2.73 | 2.74 | 2.83 | 2.76 |
|  | HD21 | 7.63 | 7.63 | 7.59 | 7.35 |
|  | HD22 | 6.97 | 6.97 | 7.12 | 7.14 |
|  | C | 174.9 | 174.9 | — | 175.31 |
|  | CA | 53.8 | 53.8 | — | 53.55 |
|  | CB | 39.2 | 39.2 | — | 38.68 |
|  | CG | 177.3 | 177.3 | — | 176.77 |
|  | N | 119.0 | 118.9 | — | 118.97 |
|  | ND2 | 113.3 | 113.3 | — | 112.79 |
| Mil[5] | H | — | 8.19 | — | — |
|  | HA | — | 4.11 | — | — |
|  | HB | — | 1.98 | — | — |
|  | HG12 | — | 2.10 | — | — |
|  | HG13 | — | 1.90 | — | — |
|  | HG2 | — | 0.82 | — | — |
|  | HD | — | 5.72 | — | — |
|  | HE1 | — | 5.06 | — | — |
|  | HE2 | — | 5.06 | — | — |
|  | C | — | 175.7 | — | — |
|  | CA | — | 60.8 | — | — |
|  | CB | — | 36.7 | — | — |
|  | CG1 | — | 38.8 | — | — |
|  | CG2 | — | 17.9 | — | — |
|  | CD | — | 138.2 | — | — |
|  | CE | — | 120.1 | — | — |
|  | N | — | 119.9 | — | — |

[a] Nomenclature according to IUPAC recommendations for the presentation of NMR structures of proteins and nucleic acids.
[b] Kobayashi et al. (1992) FEBS Lett. 2, 105-09.
[c] BMRB database: Statistics calculated for selected chemical shifts.
http://www.bmrb.wisc.edu/ref_info/statsel.htm

TABLE 4

Proton NOE data for Bacitracin A (in sample A) and Bacitracin J1 (in sample B). Measurements were made from NOESY experiments.

| Backbone amide proton | Observed proton Intra residue NOE | Inter residue NOE |
|---|---|---|
| Leu[3] | HA | HA of Thz[2] |
| Glu[4] | HA | HA of Leu[3] |
| Ile[5] | HA | HA of Glu[4] |
| Lys[6] | HA | HA of Ile[5] |
| Orn[7] | HA | HA of Lys[6] |
| Ile[8] | HA | HA of Orn[7] |
| Phe[9] | HA | HA of Ile[8] |
| His[10] | HA | HA of Phe[9] |
| Asp[11] | HA | HA of His[10] |
| Asn[12] | HA | HA of Asp[11] |
| Lys[6] [a] | HE2/HE3 | HA of Asn[12] |

TABLE 4-continued

Proton NOE data for Bacitracin A (in sample A) and Bacitracin J1 (in sample B). Measurements were made from NOESY experiments.

| Backbone amide proton | Observed proton Intra residue NOE | Inter residue NOE |
|---|---|---|
| Mil[5] [b] | HA | HA of Glu[4] |
| Lys[6] [b] | HA | HA of Mil[5] |

[a] Side chain amide proton.
[b] NOE data only occurring for Bacitracin J1.

TABLE 5

Inter- and intraresidue $^2J_{H,C}$-connectivities from the carbonyl carbons of Bacitracin A (in sample A) and Bacitracin J1 (in sample B). Measurements were made from HMBC experiments.

| Carbonyl carbon | Intra residue proton | Inter residue proton |
|---|---|---|
| Ile[1] [a] | HA | HA of Thz[2] |
| Thz[2] | HA | H of Leu[3] |
| Leu[3] | HA | H of Glu[4] |
| Glu[4] | HA | H of Ile[5] |
| Ile[5] | HA | H of Lys[6] |
| Lys[6] | HA | H of Orn[7] |
| Orn[7] | HA | H of Ile[8] |
| Ile[8] | HA | H of Phe[9] |
| Phe[9] | HA | H of His[10] |
| His[10] | HA | H of Asp[11] |
| Asp[11] | HA | H of Asn[12] |
| Asn[12] | HA | HZ of Lys[6] |
| Glu[4] [b] | HA | H of Mil[5] |
| Mil[5] [b] | HA | H of Lys[6] |

[a] Carbonyl carbon condensed in 2-thiazoline ring.
[b] HMBC data only occurring for Bacitracin J1.

Sample B (Bacitracin J1)

Identification of the amino acid spin-systems were done by 2D $^1$H—$^1$H chemical shift correlation experiments (DQF-COSY and TOCSY) and heteronuclear $^1$H—$^{13}$C and $^1$H—$^{15}$N chemical shift correlation (HSQC) in the $^1$H detected mode and the data are summarized in Table 3. The chemical shift data for residues Ile, Thz, Leu, Glu, Lys, Orn, Ile, Phe, His, Asp and Asn are nearly identical to the corresponding data for Bacitracin A, which indicates that the same residues are found unmodified in the main component of sample B. Noticeably, the spin-system corresponding to Ile[5] in Bacitracin A was significantly weaker in this sample compared to in sample A (recall that sample B contained about 20% Bacitracin A).

In addition to these signals, a $^3J_{H,H}$-coupled spin-system was found with resonances at δ 8.19 (backbone amide proton), 5.72, 5.06, 4.11, 2.10, 1.98, 1.90 and 0.82. HSQC cross-peaks at δ 5.72/138.2, δ 5.06/120.1, δ 4.11/60.8, δ 2.10/38.8, δ 1.90/38.8, δ 1.98/36.7 and at δ 0.82/17.9 indicated at least six CH$_x$-groups. COSY cross-peaks at δ 8.19/4.11, δ 4.11/1.98, δ 1.98/0.82 and HMBC cross-peaks at δ 8.19/60.8, δ 4.11/175.7, δ 4.11/36.7, δ 4.11/17.9, δ 0.82/60.8 and at δ 0.82/36.7 evidenced the following element —NHCH(CO)CHCH$_3$, which also was supported by the expected NOE correlations.

COSY cross-peaks at δ 2.10/1.90 and HMBC cross-peaks at δ 4.11/38.8, δ 0.82/38.8, δ 1.90/36.7 and at δ 1.90/17.9 evidenced the following element —NHCH(CO)CH(CH$_3$)CH$_2$, which also was supported by the expected NOE correlations.

COSY cross-peaks at δ 5.72/2.10, δ 5.72/1.90, δ 5.72/5.06 and HMBC cross-peaks at δ 5.72/38.8, δ 1.90/138.2, δ 5.06/38.8 and at δ 1.90/120.1 evidenced the following novel element —NHCH(CO)CH(CH$_3$)CH$_2$CH=CH$_2$, which also was supported by the expected NOE correlations. All chemical shift data for this unusual amino acid-analogue to Ile are similar to predicted data generated by ChemDraw (data not shown).

The sequence of the amino acid residues was established from 2D $^1H$—$^1H$ (NOESY, Table 4) and $^1H$—$^{13}C$ (HMBC, Table 5) correlation experiments. The amino acid sequence was found to be the same as in Bacitracin A, where the unusual Ile-analogue (called 5-Methylene-Isoleucine) replaces Ile at position 5. NMR data are thus in accordance with the results from LC-MS" and accurate mass determination, where all data indicates the presence of the following Bacitracin A-analogue in sample A:

for samples A and B, a DEPT(135) experiment was also performed on sample C (Table 6). This experiment further verified the structure of the two unusual and identical amino acid-analogues to Ile in sample C. One of these Ile-analogues was situated at the N-terminal (as indicated by its lack of visible backbone amide proton), and was correspondingly denoted 5-Methylene-Isoleucine[1]. The other Ile-analogue was situated at position 8, as evidenced by NOESY and HMBC correlations, and was therefore denoted 5-Methylene-Isoleucine[8]. NMR data are thus in accordance with the results from LC-MS" and accurate mass determination. All the data indicates the presence of two Bacitracin A-analogues

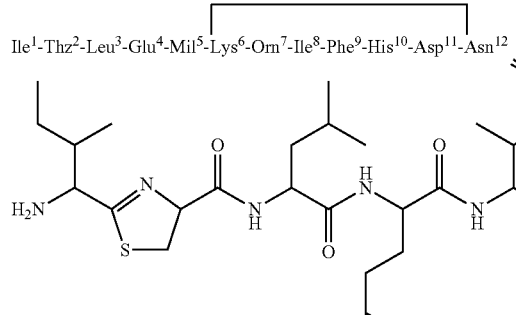

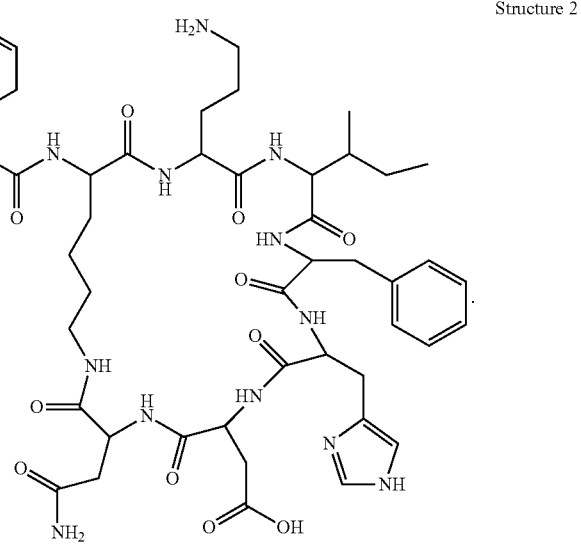

Structure 2

Bacitracin J1.

Sample C (Bacitracin J2 and Bacitracin J3)

NMR data evidenced the presence of two residues of the same unusual Ile-analogue that was present in sample B (see Table 6). In addition to the 2D experiments that were acquired in sample C, where the unusual Ile-analogue replaces Ile at position 8 in one Bacitracin A-analogue, and where the unusual Ile-analogue replaces Ile at position 1 in the second Bacitracin A-analogue:

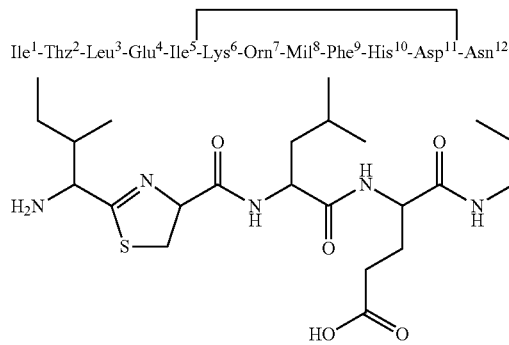

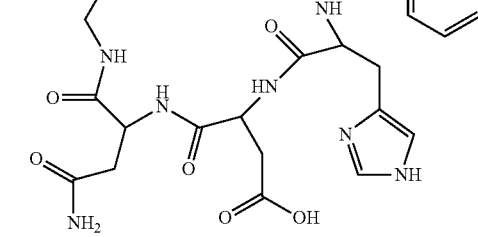

Structure 3

Bacitracin J2.

-continued

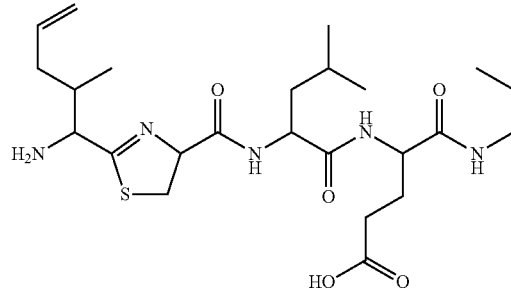
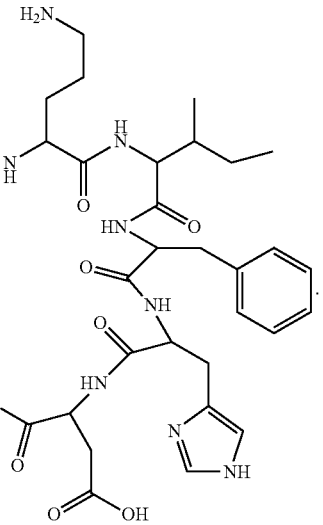

Structure 4

Bacitracin J3.

TABLE 6

$^1$H, $^{13}$C and $^{15}$N chemical shifts and DEPT(135)-data for Bacitracin J2 and Bacitracin J3 (in sample C). Data was recorded in 95% phosphate buffer pH 6.5/5% D$^2$O at 303K. Chemical shifts are reported in p.p.m., using internal 2,2-Dimethyl-2-silapentane-5-sulfonic acid (0.5 mM) as reference.

| Residue | Atom name [a] | Bacitracin J2 shift observed | Bacitracin J3 shift observed | DEPT (135) signal | DEPT (135) assignment |
|---|---|---|---|---|---|
| Mil$^8$ | H | 8.26 | | | |
| | HA | 4.12 | | | |
| | HB | 1.87 | | | |
| | HG12 | 1.99 | | | |
| | HG13 | 1.77 | | | |
| | HG2 | 0.56 | | | |
| | HD | 5.67 | | | |
| | HE1 | 5.03 | | | |
| | HE2 | 5.03 | | | |
| | C | 175.8 | | — | C |
| | CA | 60.8 | | Positive | CH |
| | CB | 36.8 | | Positive | CH |
| | CG1 | 38.8 | | Negative | CH$_2$ |
| | CG2 | 17.7 | | Positive | CH$_3$ |
| | CD | 138.6 | | Positive | CH |
| | CE | 119.7 | | Negative | CH$_2$ |
| | N | 124.5 | | | |
| Mil$^1$ | H | | — | | |
| | HA | | 4.33 | | |
| | HB | | 2.27 | | |
| | HG12 | | 2.26 | | |
| | HG13 | | 2.07 | | |
| | HG2 | | 1.06 | | |
| | HD | | 5.82 | | |
| | HE1 | | 5.16 | | |
| | HE2 | | 5.16 | | |
| | C | | 174.7 | — | C |
| | CA | | 59.6 | Positive | CH |
| | CB | | 37.9 | Positive | CH |
| | CG1 | | 38.2 | Negative | CH$_2$ |
| | CG2 | | 17.2 | Positive | CH$_3$ |
| | CD | | 138.2 | Positive | CH |
| | CE | | 120.4 | Negative | CH$_2$ |
| | N | | — | | |

[a] Nomenclature according to IUPAC recommendations for the presentation of NMR structures of proteins and nucleic acids.

Experiment 5

Potency

The antibacterial activity of samples A, B' and C' (see Table 1) was measured. The specific antibacterial activity (listed here as IU/mg), often termed potency, was measured by comparing the antibacterial activity of the unknown sample with known (standard) samples. Specifically, a Bacitracin Zinc standard was dissolved and diluted to 2.0, 1.0, and 0.5 IU bacitracin/ml in 0.07 M phosphate buffer pH 6.0. These three standard solutions were added to agar plates inoculated with the test organism, *Micrococcus luteus*. The unknown samples were dissolved, diluted and added to the same plate as the standards. After 16-24 hours at 32-37 C, the inhibition zones were measured and the unknown samples were compared to the standards. The results (reported as IU/mg) of each sample is listed in Table 7.

TABLE 7

Potency (specific antibacterial activity, IU/mg) of the isolated samples. Test organism: *Micrococcus luteus*.

| Sample | Potency (IU/mg) |
|---|---|
| A | 72 |
| B' | 53 |
| C' | 60 |

The sample A contained, as listed in Table 1, 93% (measured with HPLC at 254 nm) Bacitracin A (and no Bacitracin J1, J2 or J3). The specific antibacterial activity of Bacitracin A can then be calculated to 77.4 IU/mg. This is lower than earlier reported. Possible explanations could be water or salt content, as well as possible antagonistic effects of minor components. As samples B' and C' contain mixtures of several Bacitracins, it is not possible to report an exact specific antimicrobial activity (IU/mg) of the Bacitracin J1, J2 or J3. However, the available data strongly indicates potencies of Bacitracin J1, J2 and J3 being similar or above that of Bacitracin A. Also samples B' and C' could contain water, salt and/or components having synergistic or antagonistic effects.

The invention claimed is:
1. A compound represented by the formula

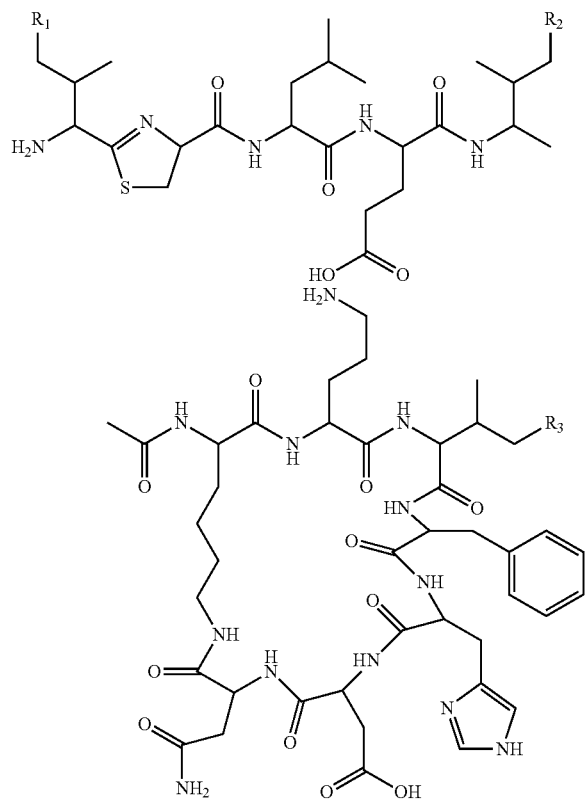

wherein
at least one of $R_1$, $R_2$ and $R_3$ is —CH=CH$_2$, and
wherein
$R_1$, $R_2$ and $R_3$ are independently —H, —CH$_3$, or CH=CH$_2$, and
salts and hydrates thereof.

2. A compound according to claim 1, wherein one of $R_1$, $R_2$ and $R_3$ is —CH$_3$.

3. A compound according to claim 1, wherein two of $R_1$, $R_2$ and $R_3$ are —CH$_3$.

4. A compound according to claim 1, wherein $R_1$ is —CH=CH$_2$.

5. A compound according to claim 1, wherein $R_2$ is —CH=CH$_2$.

6. A compound according to claim 1, wherein $R_3$ is —CH=CH$_2$.

7. A compound according to claim 1, wherein $R_1$ and $R_2$ are —CH=CH$_2$.

8. A compound according to claim 1, wherein $R_2$ and $R_3$ are —CH=CH$_2$.

9. A compound according to claim 1, wherein $R_1$ and $R_3$ are —CH=CH$_2$.

10. A compound according to claim 1, wherein $R_1$ and $R_2$ and $R_3$ are —CH=CH$_2$.

11. A composition comprising the compound of claim 1 and a second active pharmaceutical ingredient.

12. A pharmaceutical composition comprising the compound of claim 1 and one or more pharmaceutical excipients.

13. A pharmaceutical composition according to claim 12, which has therapeutic effect.

14. A method of treating a human or animal having a bacterial infection, comprising administering to the human or animal a therapeutically effective amount a compound according to claim 1 to treat a bacterial infection.

15. Method for production of compounds according to claim 1 by substituting Isoleucine or Valine with 5-Methylene-Isoleucine during in vitro Bacitracin synthesis.

* * * * *